US012760098B2

(12) United States Patent
Ge et al.

(10) Patent No.: US 12,760,098 B2
(45) Date of Patent: Oct. 13, 2026

(54) HUMANIZED CD19 ANTIBODY AND USE THEREOF

(71) Applicant: HAINAN SIMCERE ZAIMING PHARMACEUTICAL CO., LTD., Haikou (CN)

(72) Inventors: Hu Ge, Shanghai (CN); Lian Xin, Shanghai (CN)

(73) Assignee: HAINAN SIMCERE ZAIMING PHARMACEUTICAL CO., LTD., Haikou (CN)

( * ) Notice: Subject to any disclaimer, the term of this patent is extended or adjusted under 35 U.S.C. 154(b) by 656 days.

(21) Appl. No.: 18/037,574

(22) PCT Filed: Nov. 17, 2021

(86) PCT No.: PCT/CN2021/131305

§ 371 (c)(1),
(2) Date: May 18, 2023

(87) PCT Pub. No.: WO2022/105811

PCT Pub. Date: May 27, 2022

(65) Prior Publication Data

US 2023/0406922 A1 Dec. 21, 2023

(30) Foreign Application Priority Data

Nov. 20, 2020 (CN) ......................... 202011305760.5

(51) Int. Cl.
*C07K 16/28* (2006.01)

(52) U.S. Cl.
CPC ...... *C07K 16/2803* (2013.01); *C07K 2317/24* (2013.01); *C07K 2317/565* (2013.01); *C07K 2317/567* (2013.01); *C07K 2317/92* (2013.01)

(58) Field of Classification Search
None
See application file for complete search history.

(56) References Cited

U.S. PATENT DOCUMENTS

2014/0271635 A1 9/2014 Brogdon et al.

FOREIGN PATENT DOCUMENTS

| | | | | |
|---|---|---|---|---|
| CN | 102421800 | A | | 4/2012 |
| CN | 107074957 | A | | 8/2017 |
| CN | 107383196 | A | | 11/2017 |
| CN | 109879966 | A | * | 6/2019 |
| CN | 111848801 | A | | 10/2020 |
| CN | 111849913 | A | | 10/2020 |

OTHER PUBLICATIONS

Sela-Culang. The structural basis of antibody-antigen recognition. Front Immunol; 4:1-13. (Year: 2013).*

Cui, R., et al., "Humanized anti-CD19 chimeric antigen receptor-T cell therapy is safe and effective in lymphoma and leukemia patients with chronic and resolved hepatitis B virus infection," Hematological Oncology, 39: 75-86 (2021).

Nadler, L.M. et al., "B4, a human B lymphocyte-associated antigen expressed on normal, mitogen-activated, and malignant B lymphocytes," The Journal of Immunology, 131(1): 244-250 (1983).

Loken, M.R., et al., "Flow Cytometric Analysis of Human Bone Marrow. II. Normal B Lymphocyte Development," Blood, 70(5): 1316-1324 (1987).

Grossbard, M.L., et al., "Anti-B4-blocked ricin: a phase II trial of 7 day continuous infusion in patients with multiple myeloma," British Journal of Haematology, 102: 509-515 (1998).

Treon, S.P., et al., "Expression of Serotherapy Target Antigens in Waldenstrom's Macroglobulinemia: Therapeutic Applications and Considerations," Seminars in Oncology, 30(2): 248-252 (2003).

Pezzutto, A. et al., "CD19 monoclonal antibody HD37 inhibits anti-immunoglobulin-induced B cell activation and proliferation," J Immunol, 138(9): 2793-2799 (1987).

* cited by examiner

*Primary Examiner* — Samira J Jean-Louis
*Assistant Examiner* — Maureen Varina Driscoll
(74) *Attorney, Agent, or Firm* — Harness Dickey & Pierce P.L.C.

(57) ABSTRACT

The present invention discloses a humanized CD19 antibody and use thereof, in particular discloses an antibody or an antigen-binding fragment capable of binding to CD19, a multispecific antigen-binding molecule, a chimeric antigen receptor, an immune effector cell, a nucleic acid fragment, a vector, a cell, a composition, a preparation method, pharmaceutical use and a treatment method for cancer and an autoimmune disease, which are of great significance for the treatment of the cancer and the autoimmune disease.

11 Claims, 11 Drawing Sheets

Specification includes a Sequence Listing.

HUMANIZED CD19 ANTIBODY AND USE THEREOF

PRIORITY STATEMENT

This application is a national stage application under 35 U.S.C. § 371 of PCT International Application No. PCT/CN2021/131305, which has an international filing date of 17 Nov. 2021 which claims priority to Chinese Application No. 202011305760.5 filed 20 Nov. 2020. The content of each application recited above is incorporated herein by reference in its entirety.

REFERENCE TO AN ELECTRONIC SEQUENCE LISTING

This application contains references to amino acid sequences and/or nucleic acid sequences which have been submitted concurrently herewith as the sequence listing txt file entitled "SL_11_March_2026_ST25.txt", file size 46,947 Bytes (B), created on 11 Mar. 2026. The aforementioned sequence listing is hereby incorporated by reference in its entirety.

TECHNICAL FIELD

The present invention relates to the field of antibodies, in particular to a CD19 humanized antibody and use thereof.

BACKGROUND

B cells include pre-B cells (pre-B cells), early-developing B cells (i.e., immature B cells), mature B cells that differentiate into plasma cells and malignant B cells through the terminal differentiation, and the like. CD19 is highly expressed in most pre-B acute lymphocytic leukemia (Pre B ALL), non-Hodgkin's malignant lymphoma, chronic lymphocytic leukemia (CLL), prolymphocytic leukemia, hairy cell leukemia, and acute lymphocytic leukemia (ALL) and some non-acute lymphoblastic leukemias (Nadler et al., *J. Immunol.,* 131:244-250 (1983); and Loken et al., *Blood,* 70:1316-1324 (1987)). The expression of CD19 on plasma cells further suggests that CD19 can be expressed on different B cell tumors such as multiple myeloma, plasmacytoma, Waldenstrom's tumor (Grossbard et al., *Br. J. Haematol,* 102:509-15 (1998); and Treon et al., *Semin. Oncol,* 30:248-52 (2003)). CD19 is therefore considered a target for a variety of hematologic tumors. Meanwhile, studies have shown that CD19 may play a role in regulating MHC class II expression and signal transduction in vivo, and CD19 can be used as a potential immunotherapy target for autoimmune diseases.

Antibodies against CD19 are now mainly murine antibodies (mouse antibodies), such as the murine antibody HD37 disclosed in *J Immunol.* 1987 May 1; 138 (9): 2793-9, and the drug Blinatumomab marketed by Amgen. The murine CD19 antibody FMC63 can identify the human CD19 protein, and has been selected by several companies to develop drugs and cell therapy products. For example, the murine CD19 antibody FMC63 has been used for the CD19 CAR-T already on the market. However, mouse antibodies have strong immunogenicity, which can cause a human anti-mouse antibody (HAMA) reaction, an anti-antibody reaction (AAR) and the like in clinical application, thereby resulting in shortened half life, easy clearance, and weakened therapeutic effect, and even threatening the life of patients seriously. Therefore, the successful humanization of the murine CD19 antibody FMC63 is of great significance to the further development and drug formulation of the antibody.

SUMMARY

The present invention provides a CD19 humanized antibody or an antigen-binding fragment, a multispecific antigen-binding molecule, a chimeric antigen receptor, an immune effector cell, a nucleic acid fragment, a vector, a cell, a composition, a preparation method, pharmaceutical use, and a disease treatment method.

In a first aspect, the present invention provides a humanized antibody or an antigen-binding fragment specifically binding to CD19, wherein the antibody or the antigen-binding fragment comprises a heavy chain variable region and a light chain variable region, wherein the heavy chain variable region comprises:

a. a CDR1 comprising an HCDR1 of a VH set forth in SEQ ID NO: 2 or any one of SEQ ID NOs: 8-10;
b. a CDR2 comprising an HCDR2 of a VH set forth in SEQ ID NO: 2 or any one of SEQ ID NOs: 8-10;
c. a CDR3 comprising an HCDR3 of a VH set forth in SEQ ID NO: 2 or any one of SEQ ID NOs: 8-10; and
d. framework regions comprising framework regions HFR1, HFR2, and HFR3 of IGHV2-26*01 set forth in SEQ ID NO: 3, and a framework region HFR4 of IGHJ6*01 set forth in SEQ ID NO: 4; and the light chain variable region comprises:

a. a CDR1 comprising an LCDR1 of a VL set forth in SEQ ID NO: 1 or 7;
b. a CDR2 comprising an LCDR2 of a VL set forth in SEQ ID NO: 1 or 7;
c. a CDR3 comprising an LCDR3 of a VL set forth in SEQ ID NO: 1 or 7; and
d. framework regions comprising framework regions LFR1, LFR2, and LFR3 of IGKV1-39*01 set forth in SEQ ID NO: 5, and a framework region LFR4 of IGKJ4*01 set forth in SEQ ID NO: 6.

In some specific embodiments, a sequence set forth in any one of SEQ ID NOs: 1-10 comprises CDR regions and framework regions determined according to the Kabat numbering scheme, Chothia numbering scheme, or IMGT numbering scheme, wherein optionally, according to the Kabat numbering scheme:

```
                                    (SEQ ID NO: 22)
the HCDR1 is DYGVS;

                                    (SEQ ID NO: 23)
the HCDR2 is VIWGSETTYYNSALKS;

                                    (SEQ ID NO: 24)
the HCDR3 is HYYYGGSYAMDY;

                                    (SEQ ID NO: 25)
the HFR1 is
QVTLKESGPVLVKPTETLTLTCTVSGFSLS;

                                    (SEQ ID NO: 26)
the HFR2 is WIRQPPGKALEWLA;

                                    (SEQ ID NO: 27)
the HFR3 is
RLTISKDTSKSQVVLTMTNMDPVDTATYYCAR;

                                     (SEQ ID NO: 4)
the HFR4 is WGQGTTVTVSS;
```

-continued

```
                                  (SEQ ID NO: 28)
the LCDR1 is RASQDISKYLN;

                                  (SEQ ID NO: 29)
the LCDR2 is HTSRLHS;

                                  (SEQ ID NO: 30)
the LCDR3 is QQGNTLPYT;

                                  (SEQ ID NO: 31)
the LFR1 is
DIQMTQSPSSLSASVGDRVTITC;

                                  (SEQ ID NO: 32)
the LFR2 is WYQQKPGKAPKLLIY;

                                  (SEQ ID NO: 33)
the LFR3 is
GVPSRFSGSGSGTDFTLTISSLQPEDFATYYC;
and

                                   (SEQ ID NO: 6)
the LFR4 is FGGGTKVEIK;
```

optionally, according to the Chothia numbering scheme:

```
                                  (SEQ ID NO: 34)
the HCDR1 is GVSLPDY,

                                  (SEQ ID NO: 35)
GFSLSDY,
or
                                  (SEQ ID NO: 36)
GFSLPDY;

                                  (SEQ ID NO: 37)
the HCDR2 is WGSET;

                                  (SEQ ID NO: 24)
the HCDR3 is HYYYGGSYAMDY;

                                  (SEQ ID NO: 38)
the HFR1 is
QVTLKESGPVLVKPTETLTLTCTVS;

                                  (SEQ ID NO: 39)
the HFR2 is GVSWIRQPPGKALEWLAHI;

                                  (SEQ ID NO: 40)
the HFR3 is
KSYSTSLKSRLTISKDTSKSQVV

LTMTNMDPVDTATYYCAR;

                                   (SEQ ID NO: 4)
the HFR4 is WGQGTTVTVSS;

                                  (SEQ ID NO: 28)
the LCDR1 is RASQDISKYLN;

                                  (SEQ ID NO: 29)
the LCDR2 is HTSRLHS;

                                  (SEQ ID NO: 30)
the LCDR3 is QQGNTLPYT;

                                  (SEQ ID NO: 31)
the LFR1 is
DIQMTQSPSSLSASVGDRVTITC;

                                  (SEQ ID NO: 32)
the LFR2 is WYQQKPGKAPKLLIY;

                                  (SEQ ID NO: 33)
the LFR3 is
GVPSRFSGSGSGTDFTLTISSLQPEDFATYYC;
and
```

-continued

```
                                   (SEQ ID NO: 6)
the LFR4 is FGGGTKVEIK;
```

and optionally, according to the IMGT numbering scheme:

```
                                  (SEQ ID NO: 41)
the HCDR1 is GVSLPDYG,

                                  (SEQ ID NO: 42)
GFSLSDYG,
or
                                  (SEQ ID NO: 43)
GFSLPDYG;

                                  (SEQ ID NO: 44)
the HCDR2 is IWGSETT;

                                  (SEQ ID NO: 45)
the HCDR3 is AKHYYYGGSYAMDY;

                                  (SEQ ID NO: 38)
the HFR1 is QVTLKESGPVLVKPTETLTLTCTVS;

                                  (SEQ ID NO: 46)
the HFR2 is VSWIRQPPGKALEWLAH;

                                  (SEQ ID NO: 47)
the HFR3 is
SYSTSLKSRLTISKDTSKSQVVLTMTNMDPVDTATYY;

                                   (SEQ ID NO: 4)
the HFR4 is WGQGTTVTVSS;

                                  (SEQ ID NO: 48)
the LCDR1 is QDISKY;

                                  (SEQ ID NO: 49)
the LCDR2 is HT
or
                                  (SEQ ID NO: 50)
HTS;

                                  (SEQ ID NO: 30)
the LCDR3 is QQGNTLPYT;

                                  (SEQ ID NO: 51)
the LFR1 is DIQMTQSPSSLSASVGDRVTITC;

                                  (SEQ ID NO: 52)
the LFR2 is LNWYQQKPGKAPKLLIY;

                                  (SEQ ID NO: 53)
the LFR3 is
SSLQSGVPSRFSGSGSGTDFTLTISSLQPEDFATYYC
or
                                  (SEQ ID NO: 54)
SLQSGVPSRFSGSGSGTDFTLTISSLQPEDFATYYC;
and

                                   (SEQ ID NO: 6)
the LFR4 is FGGGTKVEIK.
```

In some specific embodiments, according to numbers determined by the Kabat numbering scheme, the heavy chain variable region comprises framework regions further comprising one or more mutations selected from the following group: Q1E, F27V, S30P, T73N, and R94K; preferably comprising Q1E and R94K; or preferably comprising Q1E, S30P, and R94K; or preferably comprising Q1E, F27V, S30P, T73N, and R94K.

In some specific embodiments, according to numbers of the Kabat numbering scheme, the light chain variable region comprises framework regions further comprising one or more mutations selected from the following group: K42G, P44V, and F71Y, preferably comprising K42G, P44V, and F71Y.

In some specific embodiments, the heavy chain variable region has an amino acid sequence set forth in any one of SEQ ID NOs: 8-10, and/or the light chain variable region has an amino acid sequence set forth in SEQ ID NO: 7.

In some specific embodiments, the heavy chain variable region comprises a CDR1, a CDR2, and/or a CDR3 with sequences having at least 80%, 85%, 90%, 91%, 92%, 93%, 94%, 95%, 96%, 97%, 98%, 99%, or 100% identity to the HCDR1, the HCDR2, and/or the HCDR3, respectively; and/or the light chain variable region comprises a CDR1, a CDR2, and/or a CDR3 with sequences having at least 80%, 85%, 90%, 91%, 92%, 93%, 94%, 95%, 96%, 97%, 98%, 99%, or 100% identity to the LCDR1, the LCDR2, and/or the LCDR3, respectively.

In some specific embodiments, the heavy chain variable region comprises a CDR1, a CDR2, and/or a CDR3 with sequences having at most 6 amino acid mutations compared to the HCDR1, the HCDR2, and/or the HCDR3, respectively, wherein the mutations can be in a number selected from 0, 1, 2, 3, 4, 5, and 6; and/or the light chain variable region comprises a CDR1, a CDR2, and/or a CDR3 with sequences having at most 6 amino acid mutations compared to the LCDR1, the LCDR2, and/or the LCDR3, respectively, wherein the mutations can be in a number selected from 0, 1, 2, 3, 4, 5, and 6.

In some specific embodiments, the heavy chain variable region comprises framework regions with sequences having at least 80%, 85%, 90%, 91%, 92%, 93%, 94%, 95%, 96%, 97%, 98%, 99%, or 100% identity to the HFR1, the HFR2, the HFR3, and/or the HFR4, respectively; and/or the light chain variable region comprises framework regions with sequences having at least 80%, 85%, 90%, 91%, 92%, 93%, 94%, 95%, 96%, 97%, 98%, 99%, or 100% identity to the LFR1, the LFR2, the LFR3, and/or the LFR4, respectively.

In some specific embodiments, the heavy chain variable region comprises framework regions with sequences having at most 15 amino acid mutations compared to the HFR1, the HFR2, the HFR3, and/or the HFR4, respectively, wherein the mutations can be in a number selected from 0, 1, 2, 3, 4, 5, 6, 7, 8, 9, 10, 11, 12, 13, 14, and 15; and/or the light chain variable region comprises framework regions with sequences having at most 15 amino acid mutations compared to the LFR1, the LFR2, the LFR3, and/or the LFR4, respectively, wherein the mutations can be in a number selected from 0, 1, 2, 3, 4, 5, 6, 7, 8, 9, 10, 11, 12, 13, 14, and 15.

In some specific embodiments, the mutations can be selected from insertions, deletions, and substitutions, wherein preferably, the substitutions are conservative amino acid substitutions.

In some specific embodiments, the antibody or the antigen-binding fragment comprises or does not comprise a heavy chain constant region and/or a light chain constant region, wherein preferably, the heavy chain constant region comprises a full-length heavy chain constant region or a fragment thereof, wherein the fragment can be selected from a CH1 domain, an Fc domain, and a CH3 domain;

preferably, the heavy chain constant region and/or the light chain constant region are a human heavy chain constant region and/or a human light chain constant region, respectively;

preferably, the heavy chain constant region can be selected from an IgG heavy chain constant region, e.g., an IgG1 heavy chain constant region, an IgG2 heavy chain constant region, an IgG3 heavy chain constant region, or an IgG4 heavy chain constant region; and preferably, the heavy chain constant region is a human Ig G1 heavy chain constant region, a human IgG2 heavy chain constant region, a human IgG3 heavy chain constant region, or a human IgG4 heavy chain constant region;

and preferably, the antibody or the antigen-binding fragment lacks fucosylation.

In some specific embodiments, the antibody or the antigen-binding fragment is selected from a monoclonal antibody, a polyclonal antibody, a natural antibody, an engineered antibody, a monospecific antibody, a multispecific antibody (e.g., a bispecific antibody), a monovalent antibody, a multivalent antibody, a full-length antibody, an antibody fragment, a naked antibody, a conjugated antibody, a humanized antibody, a fully human antibody, a Fab, a Fab', a Fab'-SH, an $F(ab')_2$, an Fd, an Fv, an scFv, a diabody, and a single domain antibody.

In some specific embodiments, the antibody or the antigen-binding fragment is further conjugated to a therapeutic agent or tracer, wherein preferably, the therapeutic agent is selected from a radioisotope, a chemotherapeutic agent, and an immunomodulator, and the tracer is selected from a radiocontrast medium, a paramagnetic ion, a metal, a fluorescent label, a chemiluminescent label, an ultrasound contrast agent, and a photosensitizer.

In some specific embodiments, the antibody or the antigen-binding fragment binds to human CD19 and/or monkey CD19; and optionally, the antibody or the antigen-binding fragment binds to human CD19 with a KD value of less than 1.00E-8 M, 1.00E-9 M, 2.00E-09 M, 3.00E-9 M, 4.00E-09 M, 5.00E-09 M, 6.00E-09 M, 7.00E-09 M, 8.00E-09 M, 9.00E-09 M, 1.00E-10 M, 2.00E-10 M, 3.00E-10 M, 4.00E-10 M, 5.00E-10 M, 6.00E-10 M, 7.00E-10 M, 8.00E-10 M, 9.00E-10 M, 1.00E-11 M, 2.00E-11 M, 3.00E-11 M, 4.00E-11 M, 5.00E-11 M, 6.00E-11 M, 7.00E-11 M, 8.00E-11 M, 9.00E-11 M, 1.00E-12 M, 2.00E-12 M, 3.00E-12 M, 4.00E-12 M, 5.00E-12 M, 6.00E-12 M, 7.00E-12 M, 8.00E-12 M, or 9.00E-12 M.

In a second aspect, the present invention further discloses a multispecific antigen-binding molecule, which comprises a first antigen-binding moiety and a second antigen-binding moiety, wherein the first antigen-binding moiety comprises the antibody or the antigen-binding fragment described above, and the second antigen-binding moiety specifically binds to an antigen other than CD19 or to a CD19 epitope different from the first antigen-binding moiety, wherein preferably, the antigen is selected from CD3, CD16, CD16A, CD4, CD5, CD8, CD14, CD15, CD19, CD20, CD21, CD22, CD23, CD25, CD33, CD37, CD38, CD40, CD40L, CD46, CD52, CD54, CD66 (a-d), CD74, CD80, CD126, CD138, B7, MUC, Ia, HLA-DR, tenascin, VEGF, PIGF, ED-B fibronectin, an oncogene product, IL-2, IL-6, TRAIL-R1, and TRAIL-R2;

and preferably, the multispecific antibody is bispecific, trispecific, or tetraspecific.

In a third aspect, the present invention further discloses a chimeric antigen receptor (CAR), which comprises an extracellular antigen-binding domain, a transmembrane domain, and an intracellular domain, wherein the extracellular antigen-binding domain comprises the CD19 antibody or the antigen-binding fragment described above.

In a fourth aspect, the present invention further discloses an immune effector cell, which comprises the chimeric antigen receptor described above or a nucleic acid fragment encoding the chimeric antigen receptor described above, wherein preferably, the immune effector cell is selected from a T cell, an NK cell (natural killer cell), an NKT cell (natural killer T cell), a monocyte, a macrophage, a dendritic cell, and a mast cell, wherein the T cell can be selected from a cytotoxic T cell, a regulatory T cell (Treg), and a helper T cell; and preferably, the immune effector cell is an allogeneic immune effector cell or an autologous immune effector cell.

In a fifth aspect, the present invention further discloses an isolated nucleic acid fragment, which encodes the antibody or the antigen-binding fragment or the multispecific antigen-binding molecule or the chimeric antigen receptor described above.

In a sixth aspect, the present invention further discloses a vector, which comprises the nucleic acid fragment described above.

In a seventh aspect, the present invention further discloses a host cell, which comprises the vector described above, wherein preferably, the cell is a prokaryotic cell or a eukaryotic cell, e.g., a bacterial cell (*E. coli*), a fungal cell (yeast), an insect cell, or a mammalian cell (CHO cell line or 293T cell line); and preferably, the cell lacks a fucosyltransferase, and more preferably, the fucosyltransferase is FUT8.

In an eighth aspect, the present invention further discloses a method for preparing the antibody or the antigen-binding fragment described above or the multispecific antigen-binding molecule described above, which comprises culturing the cell described above, and isolating an antibody or an antigen-binding fragment or a multispecific antigen-binding molecule expressed by the cell.

In a ninth aspect, the present invention further discloses a method for preparing the immune effector cell described above, which comprises introducing a nucleic acid fragment encoding the CAR described above into the immune effector cell, and optionally further comprises initiating expression of the CAR described above by the immune effector.

In a tenth aspect, the present invention further discloses a pharmaceutical composition, which comprises the antibody or the antigen-binding fragment described above, the multispecific antigen-binding molecule described above, the chimeric antigen receptor described above, the immune effector cell described above, the nucleic acid fragment described above, the vector described above, or the cell described above, and preferably further comprises a pharmaceutically acceptable carrier, diluent, or adjuvant.

In an eleventh aspect, the present invention further discloses use of the antibody or the antigen-binding fragment described above, the multispecific antigen-binding molecule described above, the chimeric antigen receptor described above, the immune effector cell described above, the nucleic acid fragment described above, the vector described above, or the cell described above in the preparation of a medicament for treating cancer or an autoimmune disease, wherein preferably, the cancer is selected from lymphoma and leukemia, wherein the lymphoma or leukemia can be selected from B-cell lymphoma, non-Hodgkin's lymphoma, mantle cell lymphoma, follicular lymphoma, marginal zone lymphoma, primary mediastinal B-cell lymphoma, diffuse large B-cell lymphoma, precursor B-cell acute lymphocytic leukemia (pre-B ALL), acute lymphocytic leukemia (ALL), chronic lymphocytic leukemia, hairy cell leukemia, prolymphocytic leukemia, plasmacytoma, Waldenstrom's tumor, and multiple myeloma; and preferably, the autoimmune disease may be selected from rheumatoid arthritis, multiple sclerosis, systemic sclerosis, neuromyelitis optica spectrum disease, systemic lupus erythematosus, myasthenia gravis, and IgG4-related diseases.

In a twelfth aspect, the present invention further discloses a method for treating cancer or an autoimmune disease, which comprises administering to a subject an effective amount of the antibody or the antigen-binding fragment described above, the multispecific antigen-binding molecule described above, the chimeric antigen receptor described above, the immune effector cell described above, the nucleic acid fragment described above, the vector described above, or the cell described above, wherein preferably, the cancer is selected from lymphoma and leukemia, wherein the lymphoma or leukemia can be selected from B-cell lymphoma, non-Hodgkin's lymphoma, mantle cell lymphoma, follicular lymphoma, marginal zone lymphoma, primary mediastinal B-cell lymphoma, diffuse large B-cell lymphoma, precursor B-cell acute lymphocytic leukemia (pre-B ALL), acute lymphocytic leukemia (ALL), chronic lymphocytic leukemia, hairy cell leukemia, prolymphocytic leukemia, plasmacytoma, Waldenstrom's tumor, and multiple myeloma; and preferably, the autoimmune disease can be selected from rheumatoid arthritis, multiple sclerosis, systemic sclerosis, neuromyelitis optica spectrum disease, systemic lupus erythematosus, myasthenia gravis, and IgG4-related diseases.

In a thirteenth aspect, the present invention further discloses the antibody or the antigen-binding fragment described above, the multispecific antigen-binding molecule described above, the chimeric antigen receptor described above, the immune effector cell described above, the nucleic acid fragment described above, the vector described above, or the cell described above, for use in treating cancer or an autoimmune disease, wherein preferably, the cancer is selected from lymphoma and leukemia, wherein the lymphoma or leukemia can be selected from B-cell lymphoma, non-Hodgkin's lymphoma, mantle cell lymphoma, follicular lymphoma, marginal zone lymphoma, primary mediastinal B-cell lymphoma, diffuse large B-cell lymphoma, precursor B-cell acute lymphocytic leukemia (pre-B ALL), acute lymphocytic leukemia (ALL), chronic lymphocytic leukemia, hairy cell leukemia, prolymphocytic leukemia, plasmacytoma, Waldenstrom's tumor, and multiple myeloma; and preferably, the autoimmune disease can be selected from rheumatoid arthritis, multiple sclerosis, systemic sclerosis, neuromyelitis optica spectrum disease, systemic lupus erythematosus, myasthenia gravis, and IgG4-related diseases.

Definitions and Description

Unless otherwise defined herein, all terms herein have the meaning commonly understood by those of ordinary skill in the art.

Furthermore, unless otherwise stated herein, terms used in the singular form herein shall include the plural form, and vice versa. More specifically, as used in this specification and the appended claims, unless otherwise clearly indicated, the singular forms "a", "an", and "the" include referents in the plural form.

The terms "including", "comprising", and "having" herein are used interchangeably and are intended to indicate the inclusion of a solution, implying that there may be elements other than those listed in the solution. Meanwhile, it should be understood that the descriptions "including", "comprising", and "having" as used herein also provides the solution of "consisting of . . . ".

The term "and/or" as used herein includes the meanings of "and", "or", and "all or any other combination of elements linked by the term".

The term "CD19" (cluster of differentiation 19) herein is a surface protein expressed on B lymphocytes and follicular dendritic cells and belongs to a member of the immunoglobulin superfamily. "CD19" herein includes mature or immature full-length wild-type CD19 proteins or mutants (e.g., point mutation, insertion mutation, or deletion mutation), splice variants, orthologs, and fragments thereof. "CD19" can be derived from humans and primates, such as monkeys (e.g., rhesus monkey and cynomolgus monkey) and rodents, e.g., mice and rats. Illustratively, the amino acid sequence of the human CD19 protein can be found in NCBI: NP_001761.3, and the amino acid sequence of the monkey CD19 protein can be found in NCBI: XM_005591542.1.

The term "binding" or "specific binding" herein means that an antigen-binding molecule (e.g., an antibody) specifically binds to an antigen and substantially identical antigens, generally with high affinity, but does not bind to unrelated antigens with high affinity. Affinity is generally reflected in an equilibrium dissociation constant (KD), with lower KD indicating higher affinity. In the case of antibodies, high affinity generally means having a KD of about $10^{-7}$ M or less, about $10^{-8}$ M or less, about $1\times10^{-9}$ M or less, about $1\times10^{-10}$ M or less, $1\times10^{-11}$ M or less, or $1\times10^{-12}$ M or less. KD is calculated as follows: KD=Kd/Ka, where KD represents the dissociation rate and Ka represents the association rate. The equilibrium dissociation constant KD can be measured by methods well known in the art, such as surface plasmon resonance (e.g., Biacore) or equilibrium dialysis. Illustratively, KD can be obtained as described in Example 6 herein.

The term "antigen-binding molecule" herein is used in the broadest sense and refers to a molecule that specifically binds to an antigen. Illustratively, antigen-binding molecules include but are not limited to, antibodies or antibody mimetics. "Antibody mimetic" refers to an organic compound or a binding domain that is capable of specifically binding to an antigen, but is not structurally related to an antibody. Illustratively, antibody mimetics include but are not limited to, affibody, affitin, affilin, a designed ankyrin repeat protein (DARPin), a nucleic acid aptamer, or a Kunitz domain peptide. The term "antibody" herein is used in the broadest sense and refers to a polypeptide or a combination of polypeptides that comprises sufficient sequence from an immunoglobulin heavy chain variable region and/or sufficient sequence from an immunoglobulin light chain variable region to be capable of specifically binding to an antigen. "Antibody" herein encompasses various forms and various structures as long as they exhibit the desired antigen-binding activity. "Antibody" herein includes alternative protein scaffolds or artificial scaffolds having grafted complementarity determining regions (CDRs) or CDR derivatives. Such scaffolds include antibody-derived scaffolds comprising mutations introduced to, e.g., stabilize the three-dimensional structure of the antibody, and fully synthetic scaffolds comprising, e.g., biocompatible polymers. See, e.g., Korndorfer et al., 2003, Proteins: Structure, *Function, and Bioinformatics,* 53 (1): 121-129 (2003); and Roque et al., *Biotechnol. Prog.* 20:639-654 (2004). Such scaffolds may also include non-antibody derived scaffolds, such as scaffold proteins known in the art to be useful for grafting CDRs, including but not limited to tenascin, fibronectin, peptide aptamers, and the like.

The term "antibody" herein includes a typical "four-chain antibody", which belongs to an immunoglobulin consisting of two heavy chains (HCs) and two light chains (LCs). The heavy chain refers to a polypeptide chain consisting of, from the N-terminus to the C-terminus, a heavy chain variable region (VH), a heavy chain constant region CH1 domain, a hinge region (HR), a heavy chain constant region CH2 domain, a heavy chain constant region CH3 domain; moreover, when the antibody is of IgE isotype, the heavy chain optionally further comprises a heavy chain constant region CH4 domain. The light chain is a polypeptide chain consisting of, from the N-terminus to the C-terminus, a light chain variable region (VL) and a light chain constant region (CL). The heavy chains are connected to each other and to the light chains through disulfide bonds to form a Y-shaped structure. The heavy chain constant regions of an immunoglobulin differ in their amino acid composition and arrangement, and thus in their antigenicity. Accordingly, "immunoglobulin" herein can be divided into five classes, or isotypes of immunoglobulins, namely IgM, IgD, IgG, IgA and IgE, with their corresponding heavy chains being μ, δ, γ, α, and ε chains, respectively. The Ig of the same class can be divided into different subclasses according to the differences in the amino acid composition of the hinge regions and the number and location of disulfide bonds in the heavy chains. For example, IgG can be divided into IgG1, IgG2, IgG3, and IgG4; and IgA can be divided into IgAQ1 and IgA2. Light chains are divided into κ or λ chains according to differences in the constant regions. Each of the five classes of Ig may have a κ chain or a λ chain.

The term "antibody" herein also includes antibodies that do not comprise a light chain, e.g., heavy-chain antibodies (HCAbs) produced by *Camelus dromedarius, Camelus bactrianus, Lama glama, Lama guanicoe, Vicugna pacos*, and the like, as well as immunoglobulin new antigen receptors (IgNAR) found in Chondrichthyes such as shark.

"Antibody" herein may be derived from any animal, including but not limited to humans and non-human animals which may be selected from primates, mammals, rodents, and vertebrates, such as Camelidae species, *Lama glama, Lama guanicoe, Vicugna pacos*, sheep, rabbits, mice, rats, or Chondrichthyes (e.g., shark).

"Antibody" herein includes but is not limited to, monoclonal antibodies, polyclonal antibodies, monospecific antibodies, multispecific antibodies (e.g., bispecific antibodies), monovalent antibodies, multivalent antibodies, intact antibodies, antigen-binding fragments, naked antibodies, conjugated antibodies, humanized antibodies, or fully human antibodies.

The term "monoclonal antibody" herein refers to an antibody obtained from a population of substantially homogeneous antibodies, that is, the individual antibodies constituting the population are identical and/or bind to the same epitope, except for possible variants (e.g., containing naturally occurring mutations or arising during the production of the formulation, such variants typically being present in minor amounts). In contrast to polyclonal antibody formulations, which generally comprise different antibodies directed against different determinants (epitopes), each monoclonal antibody in a monoclonal antibody formulation is directed against a single determinant on the antigen. The modifier "monoclonal" herein is not to be construed as requiring the production of the antibody or the antigen-binding molecule by any particular method. For example, monoclonal antibodies can be prepared by a variety of techniques, including (but not limited to) a hybridoma technique, a recombinant DNA method, a phage library display technique, methods that utilize transgenic animals containing all or part of human immunoglobulin loci, and other methods known in the art.

The term "natural antibody" herein refers to an antibody that is made and/or paired by the immune system of a multicellular organism. The term "engineered antibody" herein refers to a non-natural antibody obtained by genetic engineering, antibody engineering, and the like. Illustratively, "engineered antibody" includes humanized antibodies, small molecule antibodies (e.g., scFv and the like), bispecific antibodies, and the like.

The term "monospecific" herein means having one or more binding sites, each of which binds to the same epitope of the same antigen.

The term "multispecific" means having at least two antigen-binding sites, each of which binds to a different epitope of the same antigen or a different epitope of a different antigen. Thus, terms such as "bispecific", "trispecific", and "tetraspecific" refer to the number of different epitopes to which an antibody/antigen-binding molecule can bind.

The term "valency" herein refers to the presence of a specified number of binding sites in an antibody/antigen-binding molecule. Thus, the terms "monovalent", "divalent", "tetravalent", and "hexavalent" refer to the presence of one binding site, two binding sites, four binding sites, and six binding sites, respectively, in an antibody/antigen-binding molecule.

"Full-length antibody", "complete antibody", and "intact antibody" herein are used interchangeably and refer to an antibody having a substantially similar structure to a natural antibody.

"Antigen-binding fragment" and "antibody fragment" herein are used interchangeably and do not have the entire structure of an intact antibody, but comprise only a partial or partial variant of the intact antibody that has the ability to bind to an antigen. "Antigen-binding fragment" or "antibody fragment" herein includes but is not limited to, a Fab, an $F(ab')_2$, a Fab', a Fab'-SH, an Fd, an Fv, an scFv, a diabody, and a single domain antibody.

An intact antibody is digested by papain to produce two identical antigen-binding fragments, called "Fab" fragments, each of which contains a heavy chain variable region and a light chain variable region, as well as a light chain constant region and a first heavy chain constant region (CH1). Thus, the term "Fab fragment" herein refers to an antibody fragment comprising the VL region and the constant region (CL) of a light chain, and the VH region and the first constant region (CH1) of a heavy chain. A Fab' fragment differs from the Fab fragment by the addition of a few residues (including one or more cysteines from an antibody hinge region) at the carboxyl terminus of the heavy chain CH1 region. Fab'-SH is a Fab' fragment in which the cysteine residue in the constant region of the heavy chain carries a free thiol group. $F(ab')_2$ is an antibody fragment having two antigen-binding sites (two Fab fragments) and a portion of the Fc region, produced by the pepsin treatment of an intact antibody.

The term "Fd" herein refers to an antibody consisting of VH and CH1 domains. The term "Fv" herein refers to an antibody fragment consisting of VL and VH domains of a single arm. An Fv fragment is generally considered to be the smallest antibody fragment that can form an intact antigen-binding site. It is generally believed that the six CDRs provide antigen-binding specificity to the antibody. However, even one variable region (e.g., an Fd fragment, which contains only three CDRs specific to an antigen) is capable of recognizing and binding to an antigen, although its affinity may be lower than an intact binding site.

The term "scFv" (single-chain variable fragment) herein refers to a single polypeptide chain comprising VL and VH domains, wherein the VL and VH are connected through a linker (see, e.g., Bird et al., *Science* 242:423-426 (1998); Huston et al., *Proc. Natl. Acad. Sci. USA* 85:5879-5883 (1988); and Pluckthun, *The Pharmacology of Monoclonal Antibodies*, Vol. 113, Roseburg and Moore Ed., Springer-Verlag, New York, pp 269-315 (1994)). Such scFv molecules may have a general structure: NH2-VL-linker-VH-COOH or NH2-VH-linker-VL-COOH. An appropriate linker in prior art consists of GGGGS(SEQ ID NO: 55) amino acid sequence repeats or a variant thereof. For example, a linker having the amino acid sequence $(GGGGS)_4$ (SEQ ID NO: 56) can be used, and variants thereof can also be used (Holliger et al. (1993), *Proc. Natl. Acad. Sci. USA* 90:6444-6448).

Other linkers that can be used in the present invention are described in Alfthan et al. (1995), *Protein Eng.* 8:725-731; Choi et al. (2001), *Eur. J. Immunol.* 31:94-106; Hu et al. (1996), *Cancer Res.* 56:3055-3061; Kipriyanov et al. (1999), *J. Mol. Biol.* 293:41-56; and Roovers et al. (2001), Cancer *Immunol.* In some cases, there may also be disulfide bonds between the VH and VL of the scFv, forming a disulfide-linked Fv (dsFv).

The term "diabody" herein has VH and VL domains that are expressed on a single polypeptide chain, but using a linker that is too short to allow the pairing of the two domains on the same chain, thereby forcing the domains to pair with the complementary domains of the other chain and generating two antigen-binding sites (see, e.g., Holliger P. et al., *Proc. Natl. Acad. Sci. USA* 90:6444-6448 (1993), and Poljak R. J. et al., *Structure* 2:1121-1123 (1994)).

The terms "single domain antibody" (sdAb), "VHH", and "nanobody" herein have the same meaning and are used interchangeably, and refer to an antibody consisting of only one heavy chain variable region constructed by cloning a variable region of an antibody heavy chain, which is the smallest antigen-binding fragment with complete function. Generally, a single domain antibody (VHH) consisting of only one heavy chain variable region is constructed by obtaining an antibody naturally lacking a light chain and a heavy chain constant region 1 (CH1) and then cloning a variable region of an antibody heavy chain. The single domain antibody may be derived from a Camelidae heavy chain antibody or Chondrichthyes IgNAR.

The term "naked antibody" herein refers to an antibody that is not conjugated to a therapeutic agent or tracer. The term "conjugated antibody" herein refers to an antibody conjugated to a therapeutic agent or tracer.

The term "humanized antibody" herein refers to a genetically engineered non-human antibody that has an amino acid sequence modified to increase homology to the sequence of a human antibody. Generally, all or part of the CDR regions of a humanized antibody are derived from a non-human antibody (donor antibody), and all or part of the non-CDR regions (e.g., variable region FRs and/or constant regions) are derived from a human antibody (acceptor antibody). The humanized antibody generally retains or partially retains the desired properties of the donor antibody, including but not limited to, antigen specificity, affinity, reactivity, the ability to increase the activity of immune cells, the ability to enhance an immune response, and the like.

The term "fully human antibody" herein refers to an antibody having variable regions in which both the FRs and CDRs are derived from human germline immunoglobulin sequences. Furthermore, if the antibody comprises constant regions, the constant regions are also derived from human germline immunoglobulin sequences. The fully human antibody herein may include amino acid residues not encoded by human germline immunoglobulin sequences (e.g., mutations introduced by random or site-specific mutagenesis in vitro or by somatic mutations in vivo). However, "fully human antibody" herein is not intended to include antibodies in which CDR sequences derived from the germline of another mammalian species (e.g., mouse) have been grafted onto human framework sequences. The term "variable region" herein refers to a region of the heavy or light chain of an antibody involved in the binding of the antibody to an antigen. "Heavy chain variable region" is used interchangeably with "VH" and "HCVR", and "light chain variable region" is used interchangeably with "VL" and "LCVR". Heavy and light chain variable domains (VH and VL, respectively) of natural antibodies generally have similar structures, each of which contains four conserved framework regions (FRs) and three hypervariable regions (HVRs). See, e.g., Kindt et al., *Kuby Immunology,* 6th ed., W. H. Freeman and Co., p. 91 (2007). A single VH or VL can be sufficient to provide antigen-binding specificity. The terms "complementarity determining region" and "CDR" herein are used interchangeably and generally refer to a hypervariable region (HVR) of a heavy chain variable region (VH) or a light chain variable region (VL), which is also known as the complementarity determining region because it can form precise complementarity to an epitope in a spatial structure, wherein the heavy chain variable chain CDR may be abbreviated as HCDR and the light chain variable chain CDR may be abbreviated as LCDR. The terms "framework region" or "FR region" are used interchangeably and refer to those amino acid residues of an antibody heavy chain variable region or light chain variable region, other than the CDRs, wherein the framework region of the heavy chain variable region may be abbreviated as HFR and the framework region of the light chain variable region may be abbreviated as LFR. Generally, a typical antibody variable region consists of 4 FR regions and 3 CDR regions in the following order: FR1-CDR1-FR2-CDR2-FR3-CDR3-FR4.

For further description of the CDRs, reference is made to Kabat et al., *J. Biol. Chem.,* 252:6609-6616 (1977); Kabat et al., U.S. department of health and public services, "Sequences of proteins of immunological interest" (1991); Chothia et al., *J. Mol. Biol.,* 196:901-917 (1987); Al-Lazikani B. et al., *J. Mol. Biol.,* 273:927-948 (1997); MacCallum et al., *J. Mol. Biol.,* 262:732-745 (1996); Abhinandan and Martin, *Mol. Immunol.,* 45:3832-3839 (2008); Lefranc M. P. et al., *Dev. Comp. Immunol.,* 27:55-77 (2003); and Honegger and Plückthun, *J. Mol. Biol.,* 309:657-670 (2001). "CDR" herein may be labeled and defined by any numbering scheme well known in the art, including but not limited to, Kabat numbering scheme, Chothia numbering scheme, or IMGT numbering scheme, using tool sites, including but not limited to, AbRSA site (http://cao.labshare.cn/AbRSA/cdrs.php), abYsis site (www.abysis.org/abysis/sequence_input/key_annotation/key_annotation.cgi), and IMGT site (http://www.imgt.org/3Dstructure-DB/cgi/DomainGapAlign.cgi#results). The CDR herein includes overlaps and subsets of amino acid residues defined in different ways.

The term "Kabat numbering scheme" herein generally refers to the immunoglobulin alignment and numbering scheme proposed by Elvin A. Kabat (see, e.g., Kabat et al., Sequences of Proteins of Immunological Interest, 5th Ed. Public Health Service, National Institutes of Health, Bethesda, Md., 1991).

The term "Chothia numbering scheme" herein generally refers to the immunoglobulin numbering scheme proposed by Chothia et al., which is a classical rule for identifying CDR region boundaries based on the position of structural loop regions (see, e.g., Chothia & Lesk (1987) *J. Mol. Biol.* 196:901-917; Chothia et al., (1989) *Nature* 342:878-883).

The term "IMGT numbering scheme" herein generally refers to a numbering scheme based on the international ImMunoGeneTics information system (IMGT) initiated by Lefranc et al., see Lefranc et al., *Dev. Comparat. Immunol.* 27:55-77, 2003.

Illustratively, FMC63 and humanized antibody heavy chain variable region (SEQ ID NO: 2 or 8-10) and light chain variable region (SEQ ID NO: 1 or 7) thereof, and humanized templates IGHV2-26*01 (SEQ ID NO: 3) and IGHJ6*01 (SEQ ID NO: 4), and IGKV1-39*01 (SEQ ID NO: 5) and IGKJ4*01 (SEQ ID NO: 6) are defined in terms of the CDRs and FR regions by the Kabat numbering scheme, the Chothia numbering scheme or the IMGT numbering scheme as follows (www.abysis.org/abysis/sequence_input/key_annotation/key_annotation.cgi, http://www.imgt.org/3Dstructure-DB/cgi/DomainGapAlign.cgi#results):

According to the Kabat Numbering Scheme

1. HCDR1, HCDR2, and HCDR3 of VH set forth in SEQ ID NO: 2 or 8-10:

(SEQ ID NO: 22)
HCDR1 is DYGVS;

(SEQ ID NO: 23)
HCDR2 is VIWGSETTYYNSALKS;
and (SEQ ID NO: 24)
HCDR3 is HYYYGGSYAMDY.

2. Framework regions FR1, FR2, FR3, and FR4 according to IGHV2-26*01 set forth in SEQ ID NO:

3 and IGHJ6*01 set forth in SEQ ID NO: 4:

(SEQ ID NO: 25)
HFR1 is
QVTLKESGPVLVKPTETLTLTCTVSGFSLS;

(SEQ ID NO: 26)
HFR2 is WIRQPPGKALEWLA;

(SEQ ID NO: 27)
HFR3 is
RLTISKDTSKSQVVLTMTNMDPVDTATYYCAR;
and (SEQ ID NO: 4)
HFR4 is WGQGTTVTVSS.

3. LCDR1, LCDR2, and LCDR3 of VL set forth in SEQ ID NO: 1 or 7:

(SEQ ID NO: 28)
LCDR1 is RASQDISKYLN;

(SEQ ID NO: 29)
LCDR2 is HTSRLHS;
and (SEQ ID NO: 30)
LCDR3 is QQGNTLPYT.

4. Framework regions FR1, FR2, FR3, and FR4 according to IGKV1-39*01 set forth in SEQ ID NO: 5 and IGKJ4*01 set forth in SEQ ID NO: 6:

```
                                        (SEQ ID NO: 31)
LFR1 is DIQMTQSPSSLSASVGDRVTITC;

                                        (SEQ ID NO: 32)
LFR2 is WYQQKPGKAPKLLIY;

                                        (SEQ ID NO: 33)
LFR3 is
GVPSRFSGSGSGTDFTLTISSLQPEDFATYYC;
and

                                         (SEQ ID NO: 6)
LFR4 is FGGGTKVEIK.
```

According to the Chothia Numbering Scheme

1. HCDR1, HCDR2, and HCDR3 of VH set forth in SEQ ID NO: 2 or 8-10:

```
                                        (SEQ ID NO: 34)
HCDR1 is GVSLPDY,

                                        (SEQ ID NO: 35)
GFSLSDY,
or

                                        (SEQ ID NO: 36)
GFSLPDY;

                                        (SEQ ID NO: 37)
HCDR2 is WGSET;
and

                                        (SEQ ID NO: 24)
HCDR3 is HYYYGGSYAMDY.
```

2. Framework regions FR1, FR2, FR3, and FR4 according to IGHV2-26*01 set forth in SEQ ID NO: 3 and IGHJ6*01 set forth in SEQ ID NO: 4:

```
                                        (SEQ ID NO: 38)
HFR1 is QVTLKESGPVLVKPTETLTLTCTVS;

                                        (SEQ ID NO: 39)
HFR2 is GVSWIRQPPGKALEWLAHI;

                                        (SEQ ID NO: 40)
HFR3 is KSYSTSLKSRLTISKDTSKSQVVLTMTNMDPVDTATYYCAR;
and

                                         (SEQ ID NO: 4)
HFR4 is WGQGTTVTVSS.
```

3. LCDR1, LCDR2, and LCDR3 of VL set forth in SEQ ID NO: 1 or 7:

```
                                        (SEQ ID NO: 28)
LCDR1 is RASQDISKYLN;

                                        (SEQ ID NO: 29)
LCDR2 is HTSRLHS;
and

                                        (SEQ ID NO: 30)
LCDR3 is QQGNTLPYT.
```

4. Framework regions FR1, FR2, FR3, and FR4 according to IGKV1-39*01 set forth in SEQ ID NO: 5 and IGKJ4*01 set forth in SEQ ID NO: 6:

```
                                        (SEQ ID NO: 31)
LFR1 is DIQMTQSPSSLSASVGDRVTITC;

                                        (SEQ ID NO: 32)
LFR2 is WYQQKPGKAPKLLIY;

                                        (SEQ ID NO: 33)
LFR3 is GVPSRFSGSGSGTDFTLTISSLQPEDFATYYC;
and

                                         (SEQ ID NO: 6)
LFR4 is FGGGTKVEIK.
```

According to the IMGT Numbering Scheme:

1. HCDR1, HCDR2, and HCDR3 of VH set forth in SEQ ID NO: 2 or 8-10:

```
                                        (SEQ ID NO: 41)
HCDR1 is GVSLPDYG,

                                        (SEQ ID NO: 42)
GFSLSDYG,
or

                                        (SEQ ID NO: 43)
GFSLPDYG;

                                        (SEQ ID NO: 44)
HCDR2 is IWGSETT;
and

                                        (SEQ ID NO: 45)
HCDR3 is AKHYYYGGSYAMDY;
```

2. Framework regions FR1, FR2, FR3, and FR4 according to IGHV2-26*01 set forth in SEQ ID NO: 3 and IGHJ6*01 set forth in SEQ ID NO: 4:

```
                                        (SEQ ID NO: 38)
HFR1 is QVTLKESGPVLVKPTETLTLTCTVS;

                                        (SEQ ID NO: 46)
HFR2 is VSWIRQPPGKALEWLAH;

                                        (SEQ ID NO: 47)
HFR3 is SYSTSLKSRLTISKDTSKSQVVLTMTNMDPVDTATYYC;
and

                                         (SEQ ID NO: 4)
HFR4 is WGQGTTVTVSS.
```

3. LCDR1, LCDR2, and LCDR3 of VL set forth in SEQ ID NO: 1 or 7:

```
                                        (SEQ ID NO: 48)
LCDR1 is QDISKY;

                                        (SEQ ID NO: 49)
LCDR2 is HT
or

                                        (SEQ ID NO: 50)
HTS;
and

                                        (SEQ ID NO: 30)
LCDR3 is QQGNTLPYT.
```

4. Framework regions FR1, FR2, FR3, and FR4 according to IGKV1-39*01 set forth in SEQ ID NO: 5 and IGKJ4*01 set forth in SEQ ID NO: 6:

```
                                    (SEQ ID NO: 51)
LFR1 is DIQMTQSPSSLSASVGDRVTITCRAS;

                                    (SEQ ID NO: 52)
LFR2 is LNWYQQKPGKAPKLLIY;

                                    (SEQ ID NO: 53)
LFR3 is SSLQSGVPSRFSGSGSGTDFTLTISSLQPEDFATYYC
or

                                    (SEQ ID NO: 54)
SLQSGVPSRFSGSGSGTDFTLTISSLQPEDFATYYC;
and

                                     (SEQ ID NO: 6)
LFR4 is FGGGTKVEIK.
```

The term "heavy chain constant region" herein refers to the carboxyl-terminal portion of an antibody heavy chain that is not directly involved in the binding of the antibody to an antigen, but exhibits effector functions, such as interaction with an Fc receptor, which has a more conserved amino acid sequence relative to the variable domain of the antibody. The "heavy chain constant region" comprises at least one of a CH1 domain, a hinge region, a CH2 domain, a CH3 domain, or a variant or fragment thereof. The "heavy chain constant region" includes a "full-length heavy chain constant region" having a structure substantially similar to that of a natural antibody constant region, and a "heavy chain constant region fragment" including only a portion of the full-length heavy chain constant region. Illustratively, a typical "full-length antibody heavy chain constant region" consists of the CH1 domain-hinge region-CH2 domain-CH3 domain. When the antibody is IgE, it further comprises a CH4 domain; and when the antibody is a heavy chain antibody, it does not include a CH1 domain. Illustratively, a typical "heavy chain constant region fragment" may be selected from CH1, Fc, and CH3 domains.

The term "light chain constant region" herein refers to the carboxyl-terminal portion of an antibody light chain that is not directly involved in the binding of the antibody to an antigen. The light chain constant region may be selected from a constant k domain and a constant 2 domain.

The term "Fc" herein refers to the carboxyl-terminal portion of an antibody that is formed by the hydrolysis of an intact antibody by papain, which typically comprises the CH3 and CH2 domains of the antibody. The Fc region includes, for example, an Fc region of native sequence, a recombinant Fc region, and a variant Fc region. Although the boundaries of the Fc region of an immunoglobulin heavy chain may vary slightly, the human IgG heavy chain Fc region is generally defined to stretch from an amino acid residue at position Cys226, or from Pro230, to the carboxyl terminus thereof. The C-terminal lysine of the Fc region (residue 447 according to the Kabat numbering scheme) may be removed, for example, during production or purification of the antibody, or by recombinant engineering of the nucleic acid encoding the heavy chain of the antibody, and thus, the Fc region may or may not include Lys447.

Unless otherwise stated, the numbering of amino acid residues of the "antibody" or "antigen-binding fragment" described herein is determined by the Kabat numbering scheme (see Kabat et al., Sequences of Proteins of Immunological Interest, 5th Ed. Public Health Service, National Institutes of Health, Bethesda, Md., 1991). This is illustrated below with reference to mutations in amino acid residues. For example, the F27V mutation in the heavy chain variable region refers to a mutation from F to V at amino acid residue 27 of the heavy chain as determined according to the Kabat numbering scheme described above.

The term "conserved amino acid" herein generally refers to amino acids that belong to the same class or have similar characteristics (e.g., charge, side chain size, hydrophobicity, hydrophilicity, backbone conformation, and rigidity).

Illustratively, the amino acids in each of the following groups are conserved amino acid residues of each other, and substitutions of amino acid residues within the groups are substitutions of conserved amino acids:

1) alanine (a), serine(S), and threonine (T);
2) aspartic acid (D) and glutamic acid (E);
3) asparagine (N) and glutamine (Q);
4) arginine (R), lysine (K), and histidine (H);
5) isoleucine (I), leucine (L), methionine (M), and valine (V); and
6) phenylalanine (F), tyrosine (Y), and tryptophan (W).

The term "identity" can be obtained by calculating as follows: to determine the percent "identity" of two amino acid sequences or two nucleic acid sequences, the sequences are aligned for optimal comparison purposes (e.g., for optimal alignment, gaps can be introduced in one or both of the first and second amino acid sequences or nucleic acid sequences, or non-homologous sequences can be discarded for comparison). Amino acid residues or nucleotides at corresponding amino acid positions or nucleotide positions are then compared. When a position in the first sequence is occupied by the same amino acid residue or nucleotide at the corresponding position in the second sequence, the molecules are identical at this position.

The percent identity between two sequences varies with the identical positions shared by the sequences, taking into account the number of gaps that need to be introduced and the length of each gap for optimal alignment of the two sequences.

A mathematical algorithm can be used to compare two sequences and calculate the percent identity between the sequences. For example, the percent identity between two amino acid sequences is determined with the Needlema and Wunsch algorithm ((1970) *J. Mol. Biol.,* 48:444-453; available at www.gcg.com) which has been integrated into the GAP program of the GCG software package, using the Blosum 62 matrix or PAM250 matrix and gap weight of 16, 14, 12, 10, 8, 6, or 4 and length weight of 1, 2, 3, 4, 5, or 6. For another example, the percent identity between two nucleotide acid sequences is determined with the GAP program of the GCG software package (available at www.gcg.com), using the NWSgapdna.CMP matrix and gap weight of 40, 50, 60, 70 or 80 and length weight of 1, 2, 3, 4, 5 or 6. A particularly preferred parameter set (and one that should be used unless otherwise stated) is a Blosum 62 scoring matrix with a gap penalty of 12, a gap extension penalty of 4, and a frameshift gap penalty of 5.

The percent identity between two amino acid sequences or nucleotide sequences can also be determined with a PAM120 weighted remainder table, a gap length penalty of 12, and a gap penalty of 4, using the E. Meyers and W. Miller algorithm ((1989) CABIOS, 4:11-17) which has been incorporated into the ALIGN program (version 2.0).

Additionally or alternatively, the nucleic acid sequences and protein sequences described herein can be further used as "query sequences" to perform searches against public databases to, e.g., identify other family member sequences or related sequences. For example, such searches can be performed using the NBLAST and XBLAST programs (version 2.0) of Altschul et al., (1990) *J. Mol. Biol.,* 215: 403-410. BLAST nucleotide searches can be performed using the NBLAST program, with a score of 100 and a word length of 12, to obtain nucleotide sequences homologous to the nucleic acid (SEQ ID NO: 1) molecule of the present invention. BLAST protein searches can be performed using the XBLAST program, with a score of 50 and a word length of 3, to obtain amino acid sequences homologous to the protein molecule of the present invention. To obtain gapped alignment results for comparison purposes, gapped BLAST can be used as described in Altschul et al. (1997) *Nucleic Acids Res.* 25:3389-3402. When using the BLAST and gapped BLAST programs, the default parameters of the respective programs (e.g., XBLAST and NBLAST) can be used. See www.ncbi.nlm.nih.gov. The term "chimeric antigen receptor (CAR)" herein refers to an artificial cell surface receptor engineered to express on an immune effector cell and specifically bind to an antigen, which comprises at least (1) an extracellular antigen-binding domain, e.g., a variable heavy or light chain of an antibody, (2) a transmembrane domain that anchors the CAR into the immune effector cell, and (3) an intracellular signaling domain. The CAR is capable of redirecting T cells and other immune effector cells to a selected target, e.g., a cancer cell, in a non-MHC-restricted manner using the extracellular antigen-binding domain.

The term "nucleic acid" herein includes any compound and/or substance that comprises a polymer of nucleotides. Each nucleotide consists of a base, in particular a purine or pyrimidine base (i.e., cytosine (C), guanine (G), adenine (a), thymine (T), or uracil (U)), a sugar (i.e., deoxyribose or ribose), and a phosphate group. Generally, a nucleic acid molecule is described as a sequence of bases, whereby the bases represent the primary structure (linear structure) of the nucleic acid molecule. The sequence of bases is generally expressed as 5' to 3'. In this context, the term "nucleic acid molecule" encompasses deoxyribonucleic acid (DNA), including, e.g., complementary DNA (cDNA) and genomic DNA; ribonucleic acid (RNA), in particular the synthetic form of messenger RNA (mRNA), DNA or RNA; and polymers comprising a mixture of two or more of these molecules. The nucleic acid molecule may be linear or cyclic. Furthermore, the term "nucleic acid molecule" includes both sense and antisense strands, as well as single- and double-stranded forms. Moreover, the nucleic acid molecules described herein may contain naturally occurring or non-naturally occurring nucleotides. Examples of non-naturally occurring nucleotides include modified nucleotide bases having derived sugar or phosphate backbone linkages or chemically modified residues. The nucleic acid molecule also encompasses DNA and RNA molecules suitable for use as vectors for direct expression of the antibodies of the present invention in vitro and/or in vivo, e.g., in a host or patient. Such DNA (e.g., cDNA) or RNA (e.g., mRNA) vectors may be unmodified or modified. For example, mRNA can be chemically modified to enhance the stability of the RNA vector and/or the expression of the encoded molecule so that the mRNA can be injected into a subject to produce antibodies in vivo (see, e.g., Stadler et al., *Nature Medicine* 2017, published online, Jun. 12, 2017, doi: 10.1038/nm.4356 or EP 2 101 823 B1). An "isolated" nucleic acid herein refers to a nucleic acid molecule that has been separated from components of its natural environment. The isolated nucleic acid includes a nucleic acid molecule contained in a cell that generally contains the nucleic acid molecule, but the nucleic acid molecule is present extrachromosomally or at a chromosomal location different from its natural chromosomal location.

The term "vector" herein refers to a nucleic acid molecule capable of amplifying another nucleic acid to which it has been linked. The term includes vectors that serve as self-replicating nucleic acid structures as well as vectors integrated into the genome of a host cell into which they have been introduced. Certain vectors are capable of directing the expression of nucleic acids to which they are operably linked. Such vectors are called "expression vectors" herein.

The term "host cell" herein refers to a cell into which an exogenous nucleic acid has been introduced, including the progeny of such a cell. Host cells include "transformants" and "transformed cells", which include primary transformed cells and progenies derived therefrom, regardless of the number of passages. Progenies may not be exactly the same as parent cells in terms of nucleic acid content, and may contain mutations. Mutant progenies having the same function or biological activity that are screened or selected from the primary transformed cells are included herein.

The term "pharmaceutical composition" herein refers to a formulation that exists in a form allowing the biological activity of the active ingredient contained therein to be effective, and does not contain additional ingredients having unacceptable toxicity to a subject to which the pharmaceutical composition is administered.

The term "treatment" herein refers to surgical or therapeutic treatment for the purpose of preventing, slowing (reducing) the progression of an undesired physiological or pathological change, e.g., cancer or an autoimmune disease, in a subject being treated. Beneficial or desired clinical results include, but are not limited to, alleviation of symptoms, decrease of severity of disease, stabilization (i.e., not worsening) of state of disease, delay or slowing of disease progression, amelioration or palliation of state of disease, and remission (whether partial or complete), whether detectable or undetectable. Subjects in need of treatment include subjects already suffering from a disorder or disease as well as subjects susceptible to a disorder or disease or subjects for whom prevention of a disorder or disease is intended. When referring to terms such as slow, moderate, reduce, ameliorate, and alleviate, their meanings also include elimination, disappearance, nonoccurrence, etc.

The term "subject" herein refers to an organism that receives treatment for a particular disease or disorder described herein. Examples of subjects and patients include mammals, such as humans, primates (e.g., monkey), or non-primate mammals, that are being treated for a disease or disorder. The term "effective amount" herein refers to an amount of a therapeutic agent that is effective to prevent or alleviate symptoms of a disease or the progression of the disease when administered to a cell, tissue or subject alone or in combination with another therapeutic agent. "Effective amount" also refers to an amount of a compound that is sufficient to alleviate symptoms, e.g., to treat, cure, prevent, or alleviate the associated medical disorder, or to increase the rate at which such disorder is treated, cured, prevented, or alleviated. When the active ingredient is administered alone to an individual, a therapeutically effective dose refers to the amount of the ingredient alone. When a combination is used, a therapeutically effective dose refers to the combined amounts of the active ingredients that produce the therapeutic effect, whether administered in combination, sequentially or simultaneously. The term "autoimmune disease" herein refers to a disorder of cellular, tissue and/or organ damage resulting from an immune response in a subject to its own cells, tissue and/or organ.

The term "cancer" herein refers to or describes a physiological condition in mammals that is typically characterized by unregulated cell growth. Included in this definition are benign and malignant cancers.

The term "tumor" or "neoplasm" herein refers to all neoplastic cell growth and proliferation, whether malignant or benign, and all pre-cancerous and cancerous cells and tissues. The terms "cancer" and "tumor" are not mutually exclusive when referred to herein.

The term "$EC_{50}$" herein refers to the half maximum effective concentration, which includes the antibody concentration that induces a halfway response between the baseline and maximum after a specified exposure time. $EC_{50}$ essentially represents the antibody concentration by which 50% of its maximum effect is observed, and can be measured by methods known in the art.

Beneficial Effects

Compared with the prior art, the technical solutions of the present invention have at least one of the following beneficial effects:

1. Compared with the murine FMC63 antibody, the humanized antibodies described herein not only have the ability to bind to CD19, but also reduce the immunogenicity, which is beneficial to reducing the risk of immunological rejection of human subjects in use.
2. In terms of binding to human CD19 and/or monkey CD19, it is unexpectedly found that the humanized antibodies described herein are comparable or superior to their parent murine antibody FMC63, and are superior to a conventional humanized antibody (the binding ability of the conventional humanized antibody is 2-3 times lower than that of the parent murine antibody).
3. The humanized antibodies described herein show good binding ability to human CD19 and/or monkey CD19, which is favorable for improving the treatment effect and/or carrying out preclinical animal experiments.

DETAILED DESCRIPTION

Figure 1:
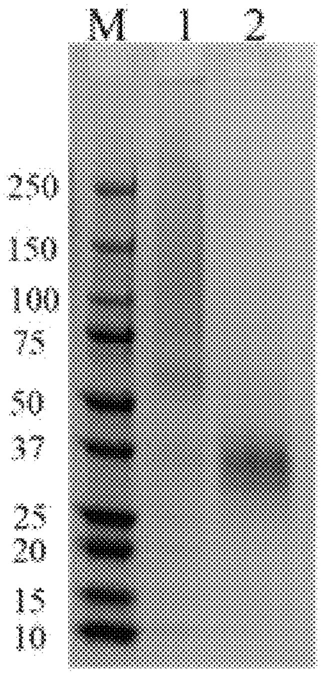
FIG. 1 shows assay results for a human CD19 exon1-3-his protein sample by SDS-PAGE reducing gel and non-reducing gel, wherein Lane M is a protein marker, Lane 1 is a non-reducing condition, and Lane 2 is a reducing condition.

The present invention is further described below with reference to specific examples, and the advantages and features of the present invention will become more apparent with the description. Experimental procedures without specified conditions in the examples are conducted according to conventional conditions or conditions recommended by the manufacturers. Reagents or instruments without specified manufacturers used herein are conventional products that are commercially available.

The examples are exemplary only and do not limit the scope of the present invention in any way. It will be understood by those skilled in the art that various changes or substitutions in form and details may be made to the technical solutions of the present invention without departing from the spirit and scope of the present invention, and that these changes and substitutions shall fall within the scope of the present invention.

Example 1. Humanization of Antibody FMC63

1.1 Humanization Design for Murine Antibody FMC63

By alignment with the IMGT (http://imgt.cines.fr) human antibody heavy and light chain variable region germline gene database, IGKV1-39*01 and IGKJ4*01 were selected as the humanized light chain template for FMC63, and IGHV2-26*01 and IGHJ6*01 were selected as the humanized heavy chain template for FMC63. The CDRs of the murine antibody were grafted onto the corresponding human templates, respectively, to form variable region sequences in the order of FR1-CDR1-FR2-CDR2-FR3-CDR3-FR4, and individual amino acid residues in the framework sequences were subjected to back mutation and hot spot mutation (see Table 1 for details). The amino acid residue sequence numbers, CDR regions, and FR regions of the antibodies of this example were determined by the Kabat numbering scheme.

TABLE 1

| Back mutation and hot spot mutation design for humanized antibodies of FMC63 | | | |
|---|---|---|---|
| VL | | VH | |
| FMC63.VL2 | Graft(IGKV1-39*01 + IGKJ4*01) + K42G, P44V, F71Y | FMC63.VH5 | Graft(IGHV2-26*01 + IGHJ6*01) + Q1E, R94K |
| | | FMC63.VH6 | Graft(IGHV2-26*01 + IGHJ6*01) + Q1E, S30P, R94K |
| | | FMC63.VH7 | Graft(IGHV2-26*01 + IGHJ6*01) + Q1E, F27V, S30P, T73N, R94K |

Note:
Grafted denotes that the CDRs of the murine antibody are grafted onto the human germline FR region sequences; and K42G denotes that K at position 42 of Grafted is back-mutated to G, and so on for others.

The mutation design for the light and heavy chain variable regions of the humanized antibodies of FMC63 in Table 1 above was subjected to a cross combination to finally obtain various humanized antibodies of FMC63 (see Table 2).

TABLE 2

| Corresponding amino acid sequences of variable regions of humanized antibodies of FMC63 | | | |
|---|---|---|---|
| | FMC63.VH5 | FMC63.VH6 | FMC63.VH7 |
| FMC63.VL2 | FMC63.25 | FMC63.26 | FMC63.27 |

Note:
FMC63.25 denotes that the humanized antibody FMC63.25 of FMC63 has a light chain variable region as shown in FMC63.VL2 and a heavy chain variable region as shown in FMC63.VH5, and so on for others.

1.2 Specific sequences of murine FMC63 antibody, humanized templates, and variable regions of humanized antibodies of FMC63

```
Light chain variable region of FMC63 (SEQ ID NO:
1):
DIQMTQTTSSLSASLGDRVTISCRASQDISKYLNWYQQKPDGTVKLLIY

HTSRLHSGVPSRFSGSGSGTDYSLTISNLEQEDIATYFCQQGNTLPYTF

GGGTKLEIT.

Heavy chain variable region of FMC63 (SEQ ID NO:
2):
EVKLQESGPGLVAPSQSLSVTCTVSGVSLPDYGVSWIRQPPRKGLEWLG

VIWGSETTYYNSALKSRLTIIKDNSKSQVFLKMNSLQTDDTAIYYCAKH

YYYGGSYAMDYWGQGTSVTVS.

IGHV2-26*01 (SEQ ID NO: 3):
QVTLKESGPVLVKPTETLTLTCTVSGFSLSNARMGVSWIRQPPGKALEW

LAHIFSNDEKSYSTSLKSRLTISKDTSKSQVVLTMTNMDPVDTATYYCA

RI.

IGHJ6*01 (SEQ ID NO: 4):
WGQGTTVTVSS.

IGKV1-39*01 (SEQ ID NO: 5):
DIQMTQSPSSLSASVGDRVTITCRASQSISSYLNWYQQKPGKAPKLLIY

AASSLQSGVPSRFSGSGSGTDFTLTISSLQPEDFATYYCQQSYSTP.

IGKJ4*01 (SEQ ID NO: 6):
FGGGTKVEIK.
```

-continued

```
Amino acid sequence of FMC63.VL2 (SEQ ID NO: 7):
DIQMTQSPSSLSASVGDRVTITCRASQDISKYLNWYQQKPGGAVKLLIY

HTSRLHSGVPSRFSGSGSGTDYTLTISSLQPEDFATYYCQQGNTLPYTF

GGGTKVEIK.

Amino acid sequence of FMC63.VH5 (SEQ ID NO: 8):
EVTLKESGPVLVKPTETLTLTCTVSGFSLSDYGVSWIRQPPGKALEWLA

VIWGSETTYYNSALKSRLTISKDTSKSQVVLTMTNMDPVDTATYYCAKH

YYYGGSYAMDYWGQGTTVTVSS.

Amino acid sequence of FMC63.VH6 (SEQ ID NO: 9):
EVTLKESGPVLVKPTETLTLTCTVSGFSLPDYGVSWIRQPPGKALEWLA

VIWGSETTYYNSALKSRLTISKDTSKSQVVLTMTNMDPVDTATYYCAKH

YYYGGSYAMDYWGQGTTVTVSS.

Amino acid sequence of FMC63.VH7 (SEQ ID NO: 10):
EVTLKESGPVLVKPTETLTLTCTVSGVSLPDYGVSWIRQPPGKALEWLA

VIWGSETTYYNSALKSRLTISKDNSKSQVVLTMTNMDPVDTATYYCAKH

YYYGGSYAMDYWGQGTTVTVSS.
```

1.3 Preparation of Humanized Antibodies of FMC63

The sequences of the heavy chain variable regions of the humanized antibodies FMC63.25, FMC63.26, and FMC63.27 of FMC63 were each cloned into an expression vector pcDNA3.4-B1HH1 containing a signal peptide and the heavy chain constant region of the murine antibody IgG1 (the sequence of the heavy chain constant region is set forth in SEQ ID NO: 11), and the sequences of the light chain variable regions were each cloned into an expression vector pcDNA3.4-B1HLK containing a signal peptide and the light chain constant region of the murine antibody IgG1 (the sequence of the light chain constant region is set forth in SEQ ID NO: 12) by Taizhou Biointron Biological Inc., to obtain the sequences of FMC63.25-mIgG1, FMC63.26-mIgG1, and FMC63.27-mIgG1, and plasmids were prepared according to established standard molecular biology methods. See Sambrook, J., Fritsch, E. F., and Maniatis, T. (1989). Molecular Cloning: A Laboratory Manual, Second Edition (Plainview, New York: Cold Spring Harbor Laboratory Press) for specific procedures. HEK293E cells (purchased from Suzhou Yiyan Biotech Co., Ltd.) were transiently transfected with the expression vectors according to PEI (purchased from Polysciences, Cat. No. 24765-1) instructions, cultured at 37° C. for 5 consecutive days using FreeStyle™ 293 (Thermofisher scientific, Cat. No. 12338018), and centrifuged to remove cell components to obtain culture supernatants containing the antibodies. The culture supernatants were each loaded on a Protein A chromatography column (the Protein A packing AT Protein A Diamond and column BXK16/26 were purchased from Bestchrom, with Cat. Nos. of AA0273 and B-1620, respectively), washed with a PBS phosphate buffer (pH 7.4), then washed with 20 mM PB, 1 M NaCl (pH 7.2), and finally subjected to elution with a citrate buffer at pH 3.4. An Fc-tagged antibody eluted from the Protein A chromatography column was collected, neutralized with 1/10 volumes of 1 M Tris at pH 8.0, and dialyzed with PBS at 4° C. overnight, and the dialyzed protein was subjected to sterile filtration through a 0.22 μM filter membrane, subpackaged, and stored at −80° C.

Heavy chain constant region of murine antibody IgG1 (SEQ ID NO: 11):

AKTTPPSVYPLAPGSAAQTNSMVTLGCLVKGYFPEPVTVTWNSGSLSS

GVHTFPAVLQSDLYTLSSSVTVPSSTWPSETVTCNVAHPASSTKVDKK

IVPRDCGCKPCICTVPEVSSVFIFPPKPKDVLTITLTPKVTCVVVDIS

KDDPEVQFSWFVDDVEVHTAQTQPREEQFNSTFRSVSELPIMHQDWLN

GKEFKCRVNSAAFPAPIEKTISKTKGRPKAPQVYTIPPPKEQMAKDKV

SLTCMITDFFPEDITVEWQWNGQPAENYKNTQPIMDTDGSYFVYSKLN

VQKSNWEAGNTFTCSVLHEGLHNHHTEKSLSHSPGK.

Light chain constant region of murine antibody IgG1 (SEQ ID NO: 12):

RADAAPTVSIFPPSSEQLTSGGASVVCFLNNFYPKDINVKWKIDGSER

QNGVLNSWTDQDSKDSTYSMSSTLTLTKDEYERHNSYTCEATHKTSTS

PIVKSFNRNEC.

Example 2. Preparation of CD19 Antigen and Positive Antibody

2.1 Preparation of Human CD19 Exon1-3-His-Tagged Protein

A nucleotide sequence encoding an amino acid sequence (SEQ ID NO: 13) of human CD19 exon1-3 Pro 20-Gln186 was cloned into a pTT5 vector (performed by General Biosystems (Anhui) Co., Ltd.), and a plasmid was prepared according to established standard molecular biology methods. The information on the corresponding amino acid sequence is shown in Table 3 below. See Sambrook, J., Fritsch, E. F., and Maniatis, T. (1989). Molecular Cloning: A Laboratory Manual, Second Edition (Plainview, New York: Cold Spring Harbor Laboratory Press) for specific procedures. HEK293E cells (purchased from Suzhou Yiyan Biotech Co., Ltd.) were transiently transfected (PEI, Polysciences, Cat. No. 24765-1) and expanded at 37° C. using FreeStyle™ 293 (Thermofisher scientific, Cat. No. 12338018). After 6 days, the cell culture medium was collected and centrifuged to remove cell components to obtain a culture supernatant containing human CD19 exon1-3. The culture supernatant was loaded on a nickel ion affinity chromatography column HisTrap™ Excel (GE Healthcare, Cat. No. GE17-3712-06), and meanwhile, the changes in UV absorbance value (A280 nm) were monitored with an ultraviolet (UV) detector. After loading, the nickel ion affinity chromatography column was washed with 20 mM PB, 0.5 M NaCl (pH 7.4) until the UV absorbance value returned to the baseline, and then subjected to gradient elution (2%, 4%, 8%, 16%, 50%, and 100%) with buffer A (20 mM PB, 0.5 M NaCl (pH 7.4)) and buffer B (20 mM PB, 0.5 M NaCl, 500 mM imidazole). A His-tagged human CD19 exon1-3 protein eluted from the nickel ion affinity chromatography column was collected and dialyzed with a PBS phosphate buffer (pH 7.4) in a refrigerator at 4° C. overnight. The dialyzed protein was subjected to sterile filtration through a 0.22 μM filter membrane, subpackaged, and stored at −80° C. to obtain a purified human CD19 exon1-3 protein. The target bands of the sample as assayed by SDS-PAGE reducing gel and non-reducing gel are shown in FIG. 1.

TABLE 3

Amino acid sequence of human CD19 exon1-3 protein

| Sequence | Sequence No. | Amino acid sequence |
|---|---|---|
| Human CD19 exon1-3 protein | SEQ ID NO: 13 | PEEPLVVKVEEGDNAVLQCLKG TSDGPTQQLTWSRESPLKPFLK LSLGLPGLGIHMRPLAIWLFIF NVSQQMGGFYLCQPGPPSEKAW QPGWTVNVEGSGELFRWNVSDL GGLGCGLKNRSSEGPSSPSGKL MSPKLYVWAKDRPEIWEGEPPC LPPRDSLNQSLSQ |

2.2 Preparation of Human CD19 Control Antibody

FMC63 and 9G8 clones are antibodies that recognize human CD19, and the antigen-binding epitopes for both are located at the membrane proximal end. The sequences of the heavy chain variable region and the light chain variable region of the FMC63 clone are obtained according to the patent WO2016033570A1, and the sequences of the heavy chain variable region and the light chain variable region of the 9G8 clone are obtained according to the patent WO2018083535. The sequences of the light chain variable regions of the FMC63 and 9G8 clones were each cloned into an expression vector pcDNA3.4-B1HH1 containing a signal peptide and the light chain constant region of the murine antibody IgG1, and the sequences of the heavy chain variable regions were each cloned into an expression vector pcDNA3.4-B1HLK containing a signal peptide and the heavy chain constant region of the murine antibody IgG1 by Taizhou Biointron Biological Inc., to obtain the sequences of FMC63-mIgG1 and 9G8-mIgG1. Hereinafter, FMC63 and 9G8 refer to FMC63-mIgG1 and 9G8-mIgG1, respectively, unless otherwise stated. Plasmids were prepared according to established standard molecular biology methods. See Sambrook, J., Fritsch, E. F., and Maniatis, T. (1989). Molecular Cloning: A Laboratory Manual, Second Edition (Plainview, New York: Cold Spring Harbor Laboratory Press) for specific procedures. HEK293E cells (purchased from Suzhou Yiyan Biotech Co., Ltd.) were transiently transfected with the expression vectors according to PEI (purchased from Polysciences, Cat. No. 24765-1) instructions, cultured at 37° C. for 5 consecutive days using FreeStyle™ 293 (Thermofisher scientific, Cat. No. 12338018), and centrifuged to remove cell components to obtain culture supernatants containing the antibodies. The culture supernatants were each loaded on a Protein A chromatography column (the Protein A packing AT Protein A Diamond and column BXK16/26 were purchased from Bestchrom, with Cat. Nos. of AA0273 and B-1620, respectively), washed with a PBS phosphate buffer (pH 7.4), then washed with 20 mM PB, 1 M NaCl (pH 7.2), and finally subjected to elution with a citrate buffer at pH 3.4. An Fc-tagged antibody eluted from the Protein A chromatography column was collected, neutralized with 1/10 volumes of 1 M Tris at pH 8.0, and dialyzed with PBS at 4° C. overnight, and the dialyzed protein was subjected to sterile filtration through a 0.22 μM filter membrane, subpackaged, and stored at −80° C.

TABLE 4

Information on heavy and light chain sequences of the anti-human CD19 antibodies FMC63-mIgG1 and 9G8-mIgG1

| Sequence | Sequence No. | Amino acid sequence |
|---|---|---|
| Heavy chain variable region of FMC63 | SEQ ID NO: 2 | EVKLQESGPGLVAPSQSLSVTCTVSGVSLPDYGVSWIRQPPRKGLEWLGV IWGSETTYYNSALKSRLTIIKDNSKSQVFLKMNSLQTDDTAIYYCAKHYY YGGSYAMDYWGQGTSVTVSS |
| Heavy chain of FMC63-mIgG1 | SEQ ID NO: 14 | EVKLQESGPGLVAPSQSLSVTCTVSGVSLPDYGVSWIRQPPRKGLEWLGV IWGSETTYYNSALKSRLTIIKDNSKSQVFLKMNSLQTDDTAIYYCAKHYY YGGSYAMDYWGQGTSVTVSSAKTTPPSVYPLAPGSAAQTNSMVTLGCL VKGYFPEPVTVTWNSGSLSSGVHTFPAVLQSDLYTLSSSVTVPSSTWPSET VTCNVAHPASSTKVDKKIVPRDCGCKPCICTVPEVSSVFIFPPKPKDVLTIT LTPKVTCVVVDISKDDPEVQFSWFVDDVEVHTAQTQPREEQFNSTFRSVS ELPIMHQDWLNGKEFKCRVNSAAFPAPIEKTISKTKGRPKAPQVYTIPPPK EQMAKDKVSLTCMITDFFPEDITVEWQWNGQPAENYKNTQPIMDTDGS YFVYSKLNVQKSNWEAGNTFTCSVLHEGLHNHHTEKSLSHSPGK |
| Light chain variable region of FMC63 | SEQ ID NO: 1 | DIQMTQTTSSLSASLGDRVTISCRASQDISKYLNWYQQKPDGTVKLLIYH TSRLHSGVPSRFSGSGSGTDYSLTISNLEQEDIATYFCQQGNTLPYTFGGG TKLEIT |
| Light chain of FMC63-mIgG1 | SEQ ID NO: 15 | DIQMTQTTSSLSASLGDRVTISCRASQDISKYLNWYQQKPDGTVKLLIYH TSRLHSGVPSRFSGSGSGTDYSLTISNLEQEDIATYFCQQGNTLPYTFGGG TKLEITRADAAPTVSIFPPSSEQLTSGGASVVCFLNNFYPKDINVKWKIDG SERQNGVLNSWTDQDSKDSTYSMSSTLTLTKDEYERHNSYTCEATHKTS TSPIVKSFNRNEC |
| Heavy chain variable region of 9G8 | SEQ ID NO: 16 | EVQLVQSGAEVKKPGESLKISCKGSGYSFTSYWIGWVRQMPGKGLEWM GIIYPGDSDTRYSPSFQGQVTISADKSISTAYLQWSSLKASDTAMYYCARG VSGIYNLHGFDIWGQGTLVTVSS |
| Heavy chain of 9G8-mIgG1 | SEQ ID NO: 17 | EVOLVQSGAEVKKPGESLKISCKGSGYSFTSYWIGWVRQMPGKGLEWM GIIYPGDSDTRYSPSFQGQVTISADKSISTAYLQWSSLKASDTAMYYCARG VSGIYNLHGFDIWGQGTLVTVSSAKTTPPSVYPLAPGSAAQTNSMVTLGC LVKGYFPEPVTVTWNSGSLSSGVHTFPAVLQSDLYTLSSSVTVPSSTWPSE TVTCNVAHPASSTKVDKKIVPRDCGCKPCICTVPEVSSVFIFPPKPKDVLTI TLTPKVTCVVVDISKDDPEVQFSWFVDDVEVHTAQTQPREEQFNSTFRSV SELPIMHQDWLNGKEFKCRVNSAAFPAPIEKTISKTKGRPKAPQVYTIPPP KEQMAKDKVSLTCMITDFFPEDITVEWQWNGQPAENYKNTQPIMDTDG SYFVYSKLNVQKSNWEAGNTFTCSVLHEGLHNHHTEKSLSHSPGK |
| Light chain variable region of 9G8 | SEQ ID NO: 18 | DIQMTQSPSSLSASVGDRVTITCRASQSISSYLNWYQQKPGKAPKLLIYAA SSLQSGVPSRFSGSGSGTDFTLTISSLQPEDFATYYCQQGRFGSPFTFGQGT KVEIK |
| Light chain of 9G8-mIgG1 | SEQ ID NO: 19 | DIQMTQSPSSLSASVGDRVTITCRASQSISSYLNWYQQKPGKAPKLLIYAA SSLQSGVPSRFSGSGSGTDFTLTISSLQPEDFATYYCQQGRFGSPFTFGQGT KVEIKRADAAPTVSIFPPSSEQLTSGGASVVCFLNNFYPKDINVKWKIDGS ERQNGVLNSWTDQDSKDSTYSMSSTLTLTKDEYERHNSYTCEATHKTST SPIVKSFNRNEC |

Example 3. Identification of Endogenously Expressing Cell Strain, and Construction and Identification of Cell Strains Overexpressing Human CD19 and Monkey CD19

3.1 Identification of Cell Strain Endogenously Expressing CD19

Figure 2A:
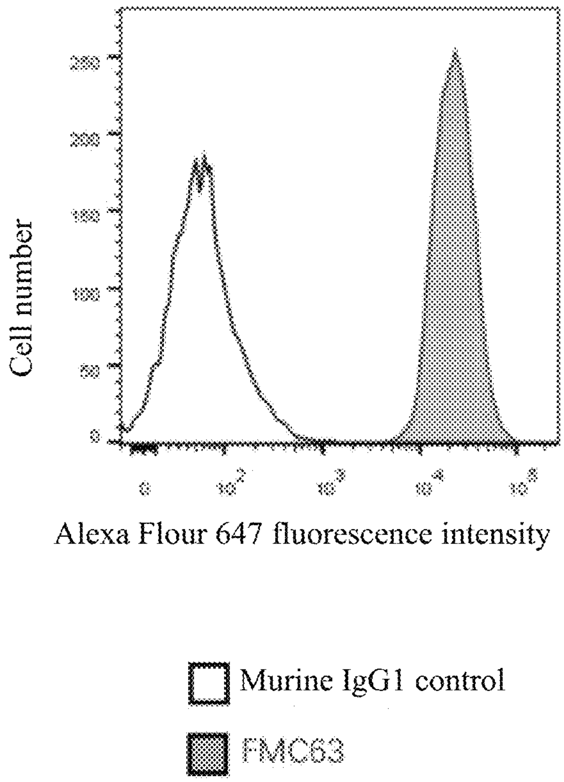
FIG. 2A shows assay results for expression level of CD19 in Raji cells using antibody FMC63 by FACS.
Figure 2B:
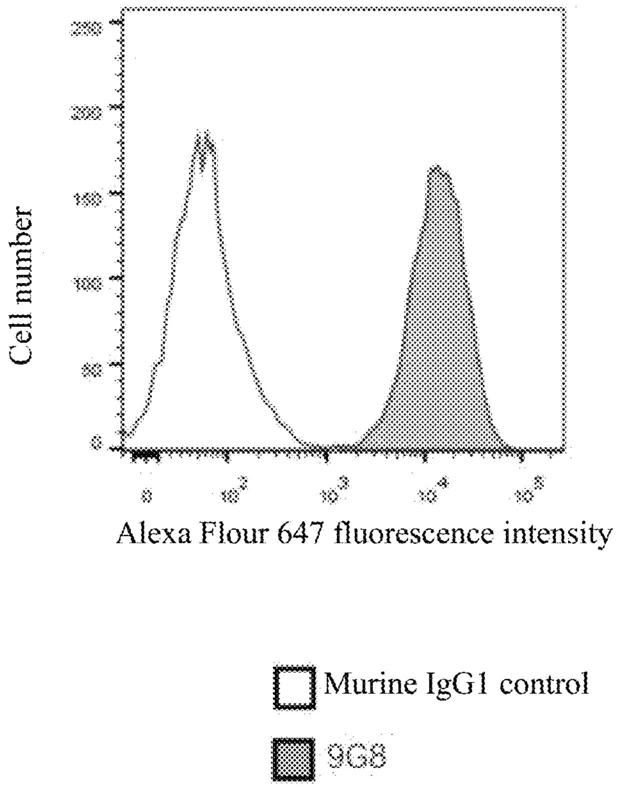
FIG. 2B shows assay results for expression level of CD19 in Raji cells using antibody 9G8 by FACS.

Raji cells (purchased from China Center for Type Culture Collection, Wuhan University) were expanded to a logarithmic growth phase in a T-25 cell culture flask, the culture supernatant was discarded by centrifugation, and the cell pellet was washed twice with PBS. The results were assayed and analyzed by FACS (FACS Canto™, purchased from BD Biosciences) using the antibodies FMC63 and 9G8 as primary antibodies and an APC-labeled secondary antibody (purchased from Biolegend, Cat. No. 409306). The analysis results are shown in Table 5 and FIGS. 2A-2B, which show that Raji cells could bind to both FMC63 and 9G8.

TABLE 5

Assay results for endogenous cell line Raji cells by FACS

| | | Mean fluorescence intensity of cells | |
|---|---|---|---|
| No. | Name of antibody | IgG subtype control | CD19 antibody |
| 1 | FMC63 | 78 | 23402 |
| 2 | 9G8 | 78 | 14600 |

3.2 Preparation of CHO-K1 Monoclonal Cell Strain Stably Transfected with Human CD19

A nucleotide sequence encoding a full-length amino acid sequence of human CD19 (NCBI: NP_001761.3, SEQ ID NO: 20) was cloned into a pcDNA3.1 vector, and a plasmid was prepared (performed by General Biosystems (Anhui) Co., Ltd.). After plasmid transfection (Lipofectamine® 3000 Transfection Kit, purchased from Invitrogen, Cat. No. L3000-015) of a CHO-K1 cell line (purchased from Chinese Academy of Sciences, Shanghai Institutes for Biological Sciences), the cells were selectively cultured in a DMEM/

F12 medium containing 10 μg/mL puromycin and 10% (w/w) fetal bovine serum for 2 weeks, and positive monoclonal cells were sorted on a flow cytometer FACS AriaII (BD Biosciences) using the antibody FMC63 as the primary antibody and an Alexa Fluor 647-labeled secondary antibody (Jackson, Cat. No. 109605088), added into a 96-well plate, and cultured in an incubator at 37° C. with 5% (v/v) $CO_2$. After about 2 weeks, some of the monoclonal wells were selected for expansion. The amplified clones were screened by flow cytometry. Monoclonal cell lines with better growth and higher fluorescence intensity were selected for further expansion and cryopreserved in liquid nitrogen.

Figure 3:
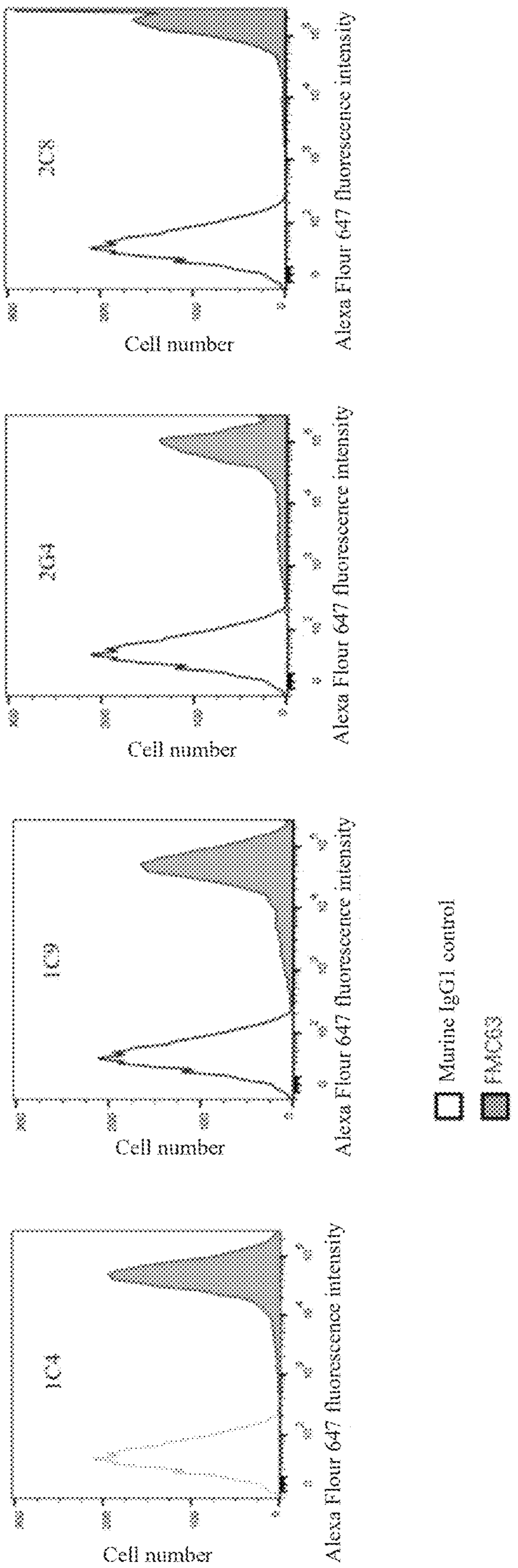
FIG. 3 shows assay results for screening for CHO-K1 cells transfected with a human CD19 protein by FACS.

The results for the selection are shown in Table 6 and FIG. 3, in which the IgG subtype control is a murine IgG1 control. In FIG. 3, the abscissa indicates the cell fluorescence intensity, and the ordinate denotes the cell number. The results in Table 6 and FIG. 3 show that CHO-K1 monoclonal cell strains with high expression of human CD19 have been prepared: CHO-K1-human CD19-2C8, CHO-K1-human CD19-1C4, CHO-K1-human CD19-2G4, and CHO-K1-human CD19 1C9. The CHO-K1-human CD19-2C8 cell strain was selected for the subsequent antibody binding assay.

```
Full-length amino acid sequence of human CD19
(SEQ ID NO: 20):
MPPPRLLFFLLFLTPMEVRPEEPLVVKVEEGDNAVLQCLKGTSDGPTQQL

TWSRESPLKPFLKLSLGLPGLGIHMRPLAIWLFIFNVSQQMGGFYLCQPG

PPSEKAWQPGWTVNVEGSGELFRWNVSDLGGLGCGLKNRSSEGPSSPSGK

LMSPKLYVWAKDRPEIWEGEPPCLPPRDSLNQSLSQDLTMAPGSTLWLSC

GVPPDSVSRGPLSWTHVHPKGPKSLLSLELKDDRPARDMWVMETGLLLPR

ATAQDAGKYYCHRGNLTMSFHLEITARPVLWHWLLRTGGWKVSAVTLAYL

IFCLCSLVGILHLQRALVLRRKRKRMTDPTRRFFKVTPPPGSGPQNQYGN

VLSLPTPTSGLGRAQRWAAGLGGTAPSYGNPSSDVQADGALGSRSPPGVG

PEEEEGEGYEEPDSEEDSEFYENDSNLGQDQLSQDGSGYENPEDEPLGPE

DEDSFSNAESYENEDEELTQPVARTMDFLSPHGSAWDPSREATSLGSQSY

EDMRGILYAAPQLRSIRGQPGPNHEEDADSYENMDNPDGPDPAWGGGGRM

GTWSTR.
```

TABLE 6

| Assay results for CHO-K1 cell line stably transfected with human CD19 protein by FACS | | | |
|---|---|---|---|
| | | Mean fluorescence intensity of cells | |
| No. | Clone No. of stably transfected cell line | IgG subtype control | CD19 antibody |
| 1 | CHO-K1-human CD19-2C8 | 50 | 131224 |
| 2 | CHO-K1-human CD19-1C4 | 50 | 45781 |
| 3 | CHO-K1-human CD19-2G4 | 50 | 44900 |
| 4 | CHO-K1-human CD19-1C9 | 50 | 31058 |

3.3 Preparation of HEK293T Cell Strain Stably Transfected with Monkey CD19

Figure 4:
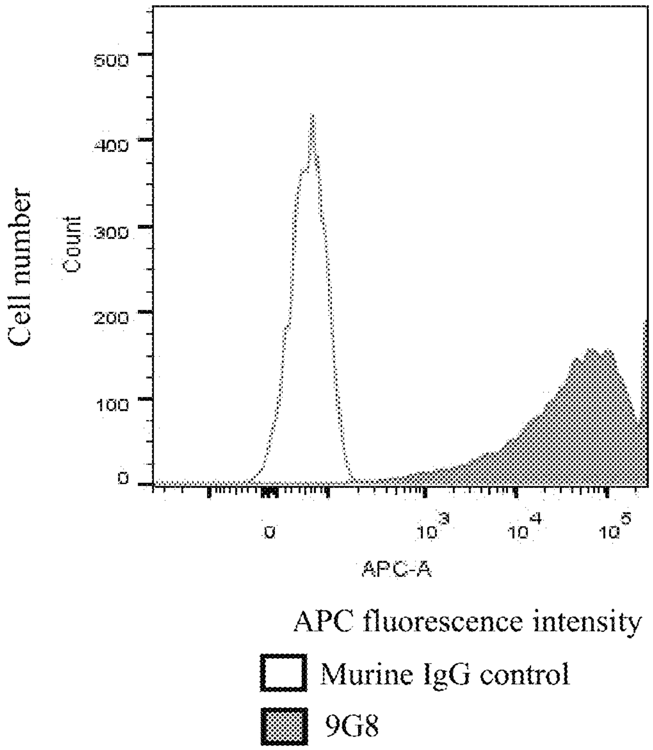
FIG. 4 shows assay results for HEK293T cells transfected with a monkey CD19 protein using antibody FMC63 by FACS.

A nucleotide sequence encoding a full-length amino acid sequence of monkey CD19 (NCBI: XM_005591542.1, SEQ ID NO: 21) was cloned into a pcDNA3.1 vector (purchased from Thermofisher scientific), and a plasmid was prepared. After plasmid transfection of the HEK293T cell line with FuGENE® HD (Promega, Cat No. E2311), the cells were selectively cultured in a DMEM medium containing 10 μg/mL puromycin and 10% (w/w) fetal bovine serum for 2 weeks, subcloned in a 96-well culture plate by a limiting dilution method, and cultured in an incubator at 37° C. with 5% (v/v) $CO_2$. After about 2 weeks, some of the polyclonal wells were selected for expansion in a 6-well plate. The amplified clones were screened by flow cytometry using a CD19 antibody 9G8 with monkey cross-activity, and cell lines with better growth and higher fluorescence intensity were selected for further expansion and cryopreserved in liquid nitrogen. The results are shown in Table 7 and FIG. 4. The assay results for HEK293T cell strains by flow cytometry using the antibody 9G8 show that positive cell peaks overexpressing monkey CD19 after puromycin screening could be used for detecting the cross-activity of the humanized antibodies of FMC63.

```
Full-length amino acid sequence of monkey CD19
(SEQ ID NO: 21):
MPPPCLLFFLLFLTPMEVRPQEPLVVKVEEGDNAVLQCLEGTSDGPTQQL

VWCRDSPFEPFLNLSLGLPGMGIRMGPLGIWLLIFNVSNQTGGFYLCQPG

LPSEKAWQPGWTVSVEGSGELFRWNVSDLGGLGCGLKNRSSEGPSSPSGK

LNSSQLYVWAKDRPEMWEGEPVCGPPRDSLNQSLSQDLTMAPGSTLWLSC

GVPPDSVSRGPLSWTHVRPKGPKSSLLSLELKDDRPDRDMWVVDTGLLLT

RATAQDAGKYYCHRGNWTKSFYLEITARPALWHWLLRIGGWKVPAVTLTY

LIFCLCSLVGILQLQRALVLRRKRKRMTDPTRRFFKVTPPPGSGPQNQYG

NVLSLPTPTSGLGRAQRWAAGLGGTAPSYGNPSSDVQVDGAVGSRSPPGA

GPEEEEGEGYEEPDSEEGSEFYENDSNFGQDQLSQDGSGYENPEDEPLGP

EDEDSFSNAESYENEDEELTQPVARTMDFLSPHGSAWDPSREATSLGSQS

YEDMRGLLYAAPQLRTIRGQPGPNHEEDADSYENMDNPDGPDPAWGGGGR

MGTWSAR.
```

TABLE 7

| Assay results of HEK293T cell line stably transfected with monkey CD19 protein by FACS | | | |
|---|---|---|---|
| | Clone No. of stably | Mean fluorescence intensity of cells | |
| No. | transfected cell line | Murine IgG control | 9G8 |
| 1 | HEK293T-monkey CD19 | 62 | 66503 |

Example 4. Identification of Humanized Antibodies of FMC63

4.1 Assay on Binding of Antibodies to CD19 Protein by Enzyme-Linked Immunosorbent Assay (ELISA)

Figure 5:
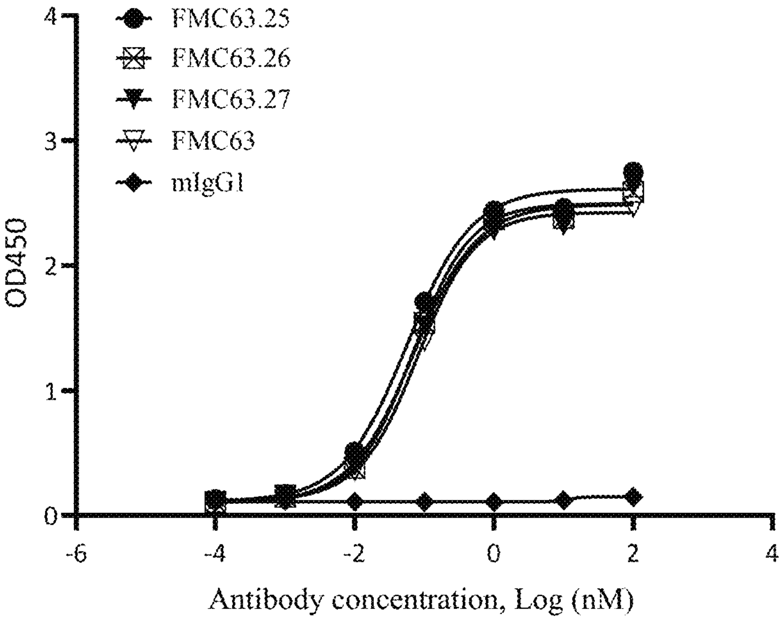
FIG. 5 shows assay results for binding reactions of humanized antibodies of FMC63 with a human CD19-His protein by ELISA.

A human CD19-his protein (purchased from ACROBiosystems, Cat. No. CD9-H52H2) was diluted with PBS to make a final concentration of 4 μg/mL, and then added into a 96-well ELISA plate at 100 μL/well. The plate was sealed with a plastic film and incubated at 4° C. overnight, wash twice with PBS the next day, and blocked at room temperature for 2 h by adding a blocking solution [PBS+2% (w/w) BSA]. The blocking solution was discarded, and 100 nM humanized antibodies of FMC63 (diluted in a gradient), FMC63, or a negative control antibody were added at 50 μL/well. After incubation for 2 h at 37° C., the plate was washed 3 times with PBS. An HRP (horseradish peroxidase)-labeled secondary antibody (purchased from Jackson Immuno, Cat. No. 115-035-003) was added. After incubation for 1 h at 37° C., the plate was washed 5 times with PBS. A TMB substrate was added at 50 μL/well. After incubation at room temperature for 10 min, a stop solution (1.0 N HCl) was added at 50 μL/well. The OD450 nm values were read on an ELISA microplate reader (Multimode Plate Reader, EnSight, purchased from Perkin Elmer). The assay results for the binding of the humanized antibodies of FMC63 to human CD19 by ELISA are shown in FIG. 5 and Table 8. Table 8 shows that the humanized antibodies of FMC63 all could bind to human CD19 at the ELISA level. The negative control antibody mIgG1 was an antibody against hen egg lysozyme, anti-hel-mIgG1 (purchased from Biointron, Cat. No. B118301), and the data in the table were OD450 nm values.

TABLE 8

Assay results for binding reactions of humanized antibodies of FMC63 with human CD19 protein by ELISA

| | OD450 Antibody concentration (nM) | | | | | | | |
|---|---|---|---|---|---|---|---|---|
| Name of antibody | 100.00 | 10.00 | 1.00 | 0.10 | 0.01 | 0.001 | 0.0001 | Blank control |
| FMC63.25 | 2.75 | 2.46 | 2.44 | 1.71 | 0.51 | 0.17 | 0.13 | 0.14 |
| FMC63.26 | 2.59 | 2.38 | 2.37 | 1.54 | 0.38 | 0.15 | 0.11 | 0.13 |
| FMC63.27 | 2.64 | 2.32 | 2.29 | 1.52 | 0.39 | 0.16 | 0.11 | 0.12 |
| FMC63 | 2.47 | 2.35 | 2.29 | 1.40 | 0.36 | 0.16 | 0.11 | 0.11 |
| mIgG1 | 0.15 | 0.12 | 0.11 | 0.11 | 0.11 | 0.12 | 0.11 | 0.12 |

4.2 Assay on Binding of Humanized Antibodies of FMC63 to Different CD19-Expressing Cells by Flow Cytometry Assay (FACS)

Figure 6A:
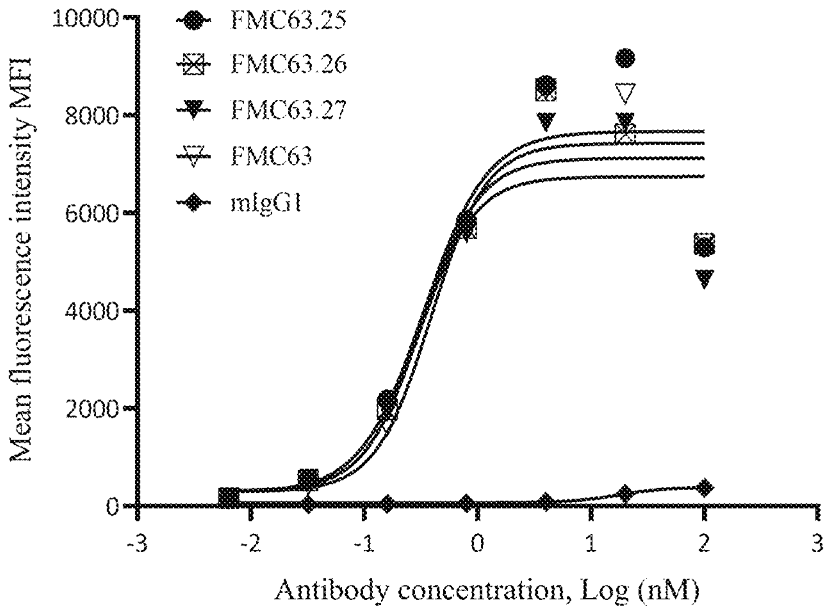
FIG. 6A shows assay results for binding reactions of humanized antibodies of FMC63 with Raji by FACS.
Figure 6B:
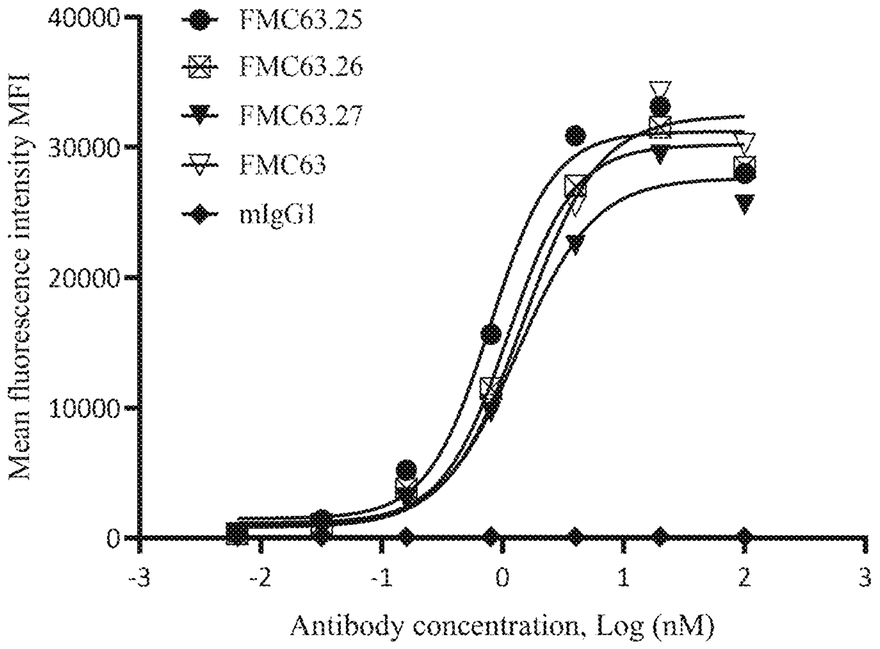
FIG. 6B shows assay results for binding reactions of humanized antibodies of FMC63 with CHO-K1-human CD19 by FACS.
Figure 6C:
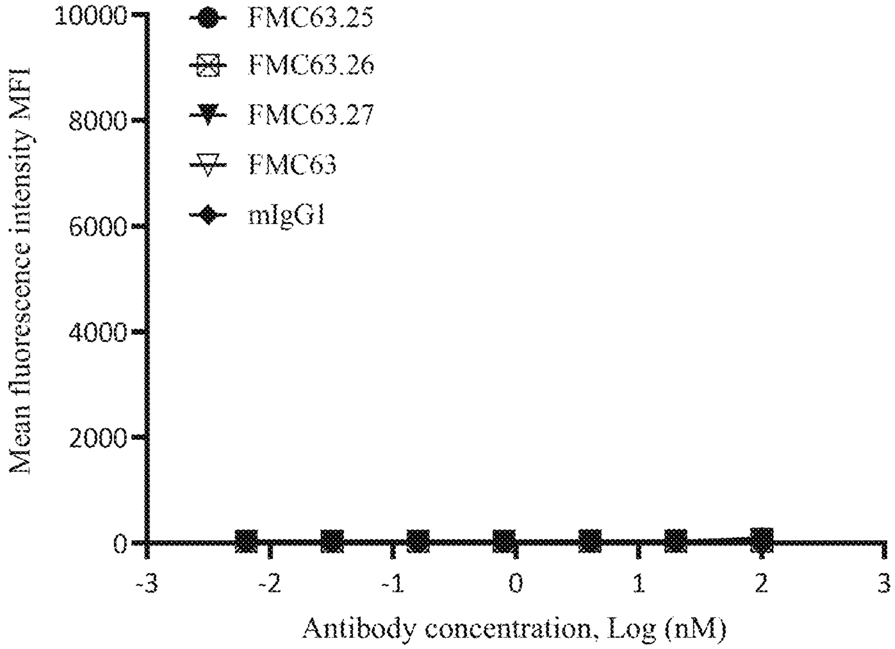
FIG. 6C shows assay results for binding reactions of humanized antibodies of FMC63 with MOLT-4 by FACS.
Figure 6D:
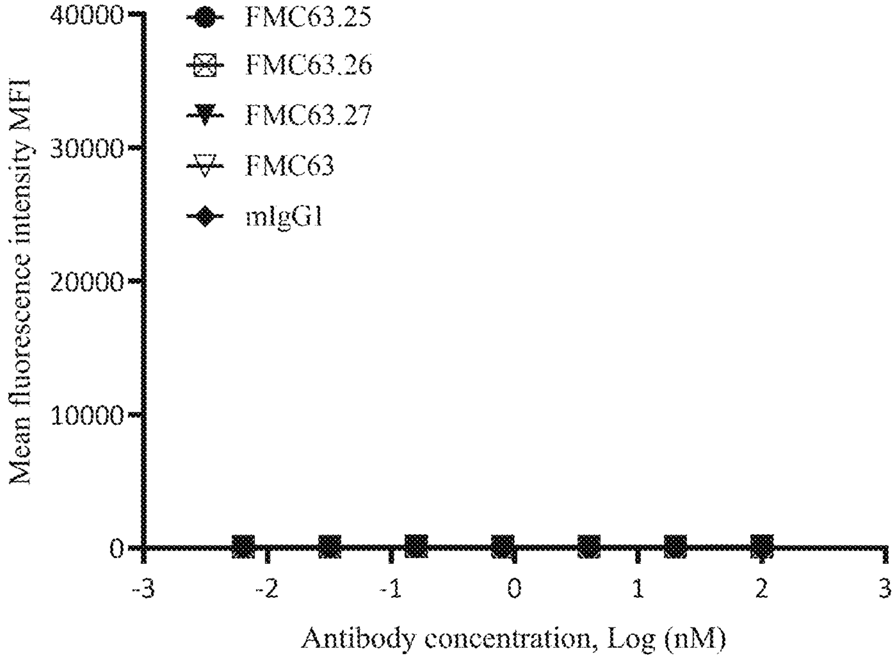
FIG. 6D shows assay results for binding reactions of humanized antibodies of FMC63 with CHO-K1 by FACS.

The desired cells were expanded to a logarithmic growth phase in a T-75 cell culture flask. For adherent cells CHO-K1, the culture medium was removed by pipetting, and the cells were washed twice with a PBS buffer, digested with trypsin, and washed twice with a PBS buffer again after the digestion was stopped. For suspension cells Raji, the medium supernatant was discarded by direct centrifugation, and the cell pellet was washed twice with PBS. After cell counting of the cells obtained in the last step, the cell pellet was resuspended to $2\times10^6$ cells/mL with a blocking solution [PBS+2% (w/w) BSA] and added into a 96-well FACS reaction plate at 50 μL/well. The test sample (humanized antibodies of FMC63, FMC63, or negative control antibody) was added at 50 μL/well, and the plate was incubated on ice for 2 h. After the plate was centrifuged and washed 3 times with a PBS buffer, an Alexa Fluor 647-labeled secondary antibody (purchased from Jackson Immuno, Cat. No. 115-605-003) was added at 50 μL/well, and the plate was incubated on ice for 1 h. After the plate was centrifuged and washed 5 times with a PBS buffer, the results were assayed and analyzed by FACS (FACS Canto™, purchased from BD Biosciences). Data analysis was performed by software (CellQuest) to obtain the mean fluorescence intensity (MFI) of the cells. Then, analysis was performed by software (GraphPad Prism8), data were fitted, and $EC_{50}$ values were calculated. The analysis results are shown in Table 9 and FIGS. 6A-6D, which show that the humanized antibodies of FMC63 all could bind to the human CD19 protein on the surface of Raji cells and CHO-K1-human CD19 cells (FIGS. 6A-6B). The same method was used to assay the binding of the humanized antibodies of FMC63 to endogenous CD19-negative MOLT-4 cells (purchased from ATCC, CRL-1582) and CHO-K1 cells. The results are shown in FIGS. 6C-6D, which show that the humanized antibodies of FMC63 all did not bind to MOLT-4 cells and CHO-K1 cells, having good specificity.

TABLE 9

Assay results for binding reactions of humanized antibodies of FMC63 to Raji and CHO-K1-human CD19 cells by FACS

| | Raji | | CHO-K1-human CD19 | |
|---|---|---|---|---|
| Name of antibody | Maximum mean fluorescence intensity | Ec50 (nM) | Maximum mean fluorescence intensity | Ec50 (nM) |
| FMC63.25 | 9168 | 0.33 | 33140 | 0.79 |
| FMC63.26 | 8502 | 0.32 | 31540 | 1.12 |
| FMC63.27 | 7844 | 0.30 | 29397 | 1.33 |
| FMC63 | 8537 | 0.39 | 34187 | 1.49 |
| mIgG1 | 382 | Negative | 102 | Negative |

Example 5. Assay on Species Cross-Binding Activity of Humanized Antibodies of FMC63

Figure 7:
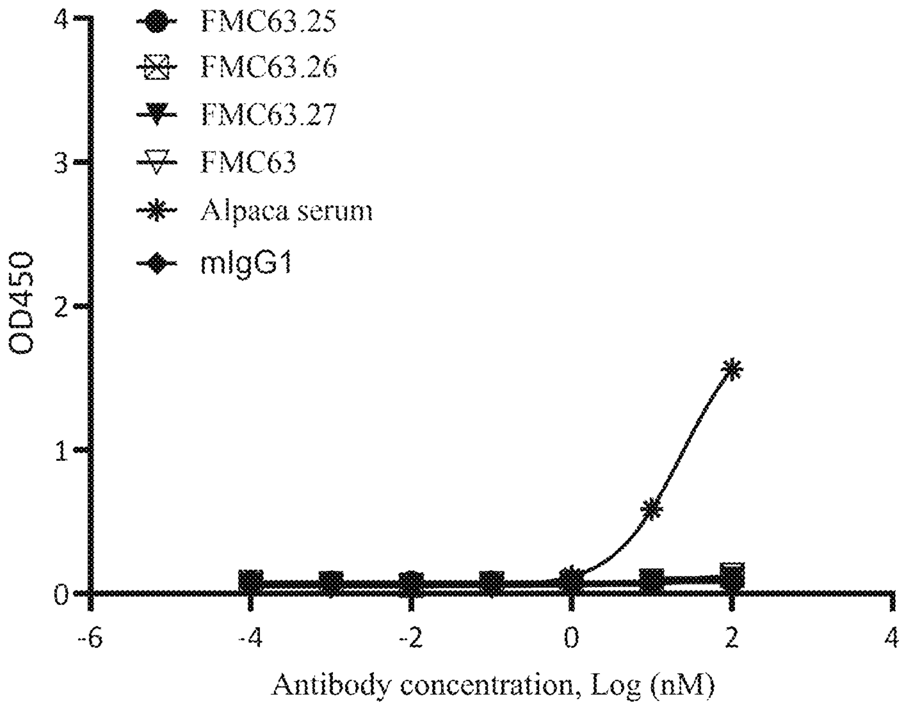
FIG. 7 shows assay results for binding reactions of humanized antibodies of FMC63 with a mouse CD19-his protein by ELISA.

5.1 Assay on Binding of Humanized Antibodies of FMC63 to CD19 Proteins of Different Species by ELISA To assay the species cross-activity of the humanized antibodies against FMC63, ELISA plates were coated with commercial murine CD19 (ACROBiosystems, Cat. No. 50510-M08H) and monkey CD19 (ACROBiosystems, Cat. No. 90051-C08H), respectively, and ELISA assays were performed according to the method described in Example 4.1. The assay results for the binding of the humanized antibodies of FMC63 to murine CD19 by ELISA are shown in FIG. 7 and Table 10. FIG. 7 and Table 10 show that the humanized antibodies of FMC63 all did not bind to murine CD19 at the ELISA level. The IgG control was mIgG1, Alpaca serum was serum from Alpaca immunized with human CD19-ECD-His and was used as a positive control (it has been verified that Alpaca serum could bind to murine CD19), and the data in the table were OD450 nm values.

TABLE 10

Assay results for binding reactions of humanized antibodies of FMC63 with murine CD19 protein by ELISA

| | OD450 Antibody concentration (nM) | | | | | | | |
|---|---|---|---|---|---|---|---|---|
| Name of antibody | 100.00 | 10.00 | 1.00 | 0.10 | 0.01 | 0.001 | 0.0001 | Blank control |
| FMC63.25 | 0.09 | 0.08 | 0.08 | 0.08 | 0.08 | 0.08 | 0.08 | 0.08 |
| FMC63.26 | 0.13 | 0.09 | 0.08 | 0.07 | 0.06 | 0.07 | 0.08 | 0.09 |
| FMC63.27 | 0.11 | 0.08 | 0.06 | 0.05 | 0.06 | 0.06 | 0.06 | 0.07 |
| FMC63 | 0.10 | 0.07 | 0.06 | 0.05 | 0.05 | 0.06 | 0.06 | 0.07 |
| Alpaca serum | 1.56 | 0.59 | 0.12 | 0.06 | 0.05 | 0.05 | 0.05 | 0.06 |
| MIgG1 | 0.11 | 0.08 | 0.06 | 0.06 | 0.06 | 0.06 | 0.07 | 0.08 |

Note:
the Alpaca serum was subjected to a 10-fold gradient dilution starting at a 1:100 dilution ratio.

Figure 8:
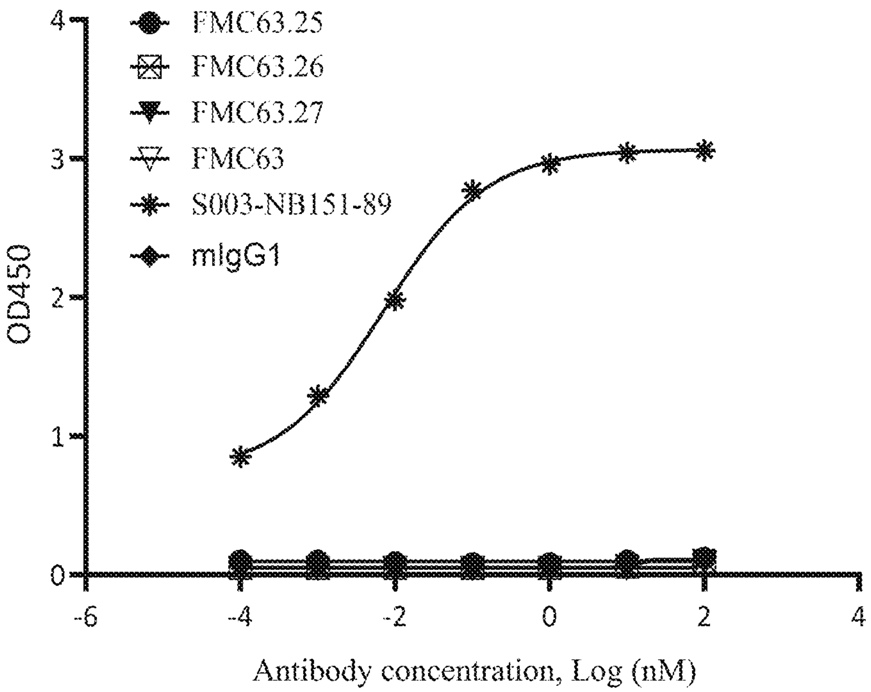
FIG. 8 shows assay results for binding reactions of humanized antibodies of FMC63 with a monkey CD19-his protein by ELISA.

The assay results for the binding of the humanized antibodies of FMC63 to monkey CD19 by ELISA are shown in FIG. 8 and Table 11. FIG. 8 and Table 11 show that the humanized antibodies of FMC63 all did not bind to monkey CD19 at the ELISA level. IgG control was mIgG1, S003-NB151-89 was a clone that is selected from a library constructed by peripheral blood collected from Alpaca immunized by human CD19-His and can bind to a monkey CD19-His protein, and was used as a positive control, and the data in the table were OD450 nm values.

TABLE 11

Assay results for binding reactions of humanized antibodies of FMC63 with monkey CD19 protein by ELISA

| Name of antibody | OD450 Antibody concentration (nM) 100.00 | 10.00 | 1.00 | 0.10 | 0.01 | 0.001 | 0.0001 | Blank control |
|---|---|---|---|---|---|---|---|---|
| FMC63.25 | 0.12 | 0.10 | 0.08 | 0.08 | 0.09 | 0.10 | 0.10 | 0.12 |
| FMC63.26 | 0.10 | 0.06 | 0.05 | 0.05 | 0.05 | 0.05 | 0.05 | 0.10 |
| FMC63.27 | 0.10 | 0.05 | 0.05 | 0.05 | 0.05 | 0.05 | 0.05 | 0.10 |
| FMC63 | 0.09 | 0.05 | 0.05 | 0.05 | 0.05 | 0.05 | 0.05 | 0.09 |
| S003-NB151-89 | 3.06 | 3.04 | 2.96 | 2.77 | 1.98 | 1.29 | 0.85 | 0.11 |
| mIgG1 | 0.11 | 0.07 | 0.05 | 0.05 | 0.05 | 0.05 | 0.06 | 0.10 |

Figure 9A:
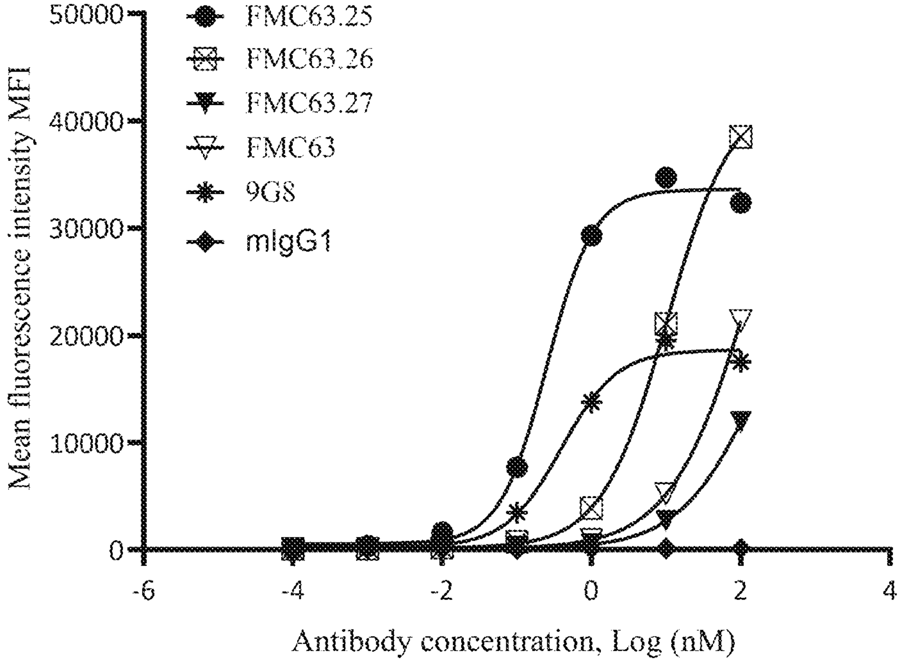
FIG. 9A shows assay results for binding reactions of humanized antibodies of FMC63 with HEK293T-monkey CD19 by FACS.
Figure 9B:
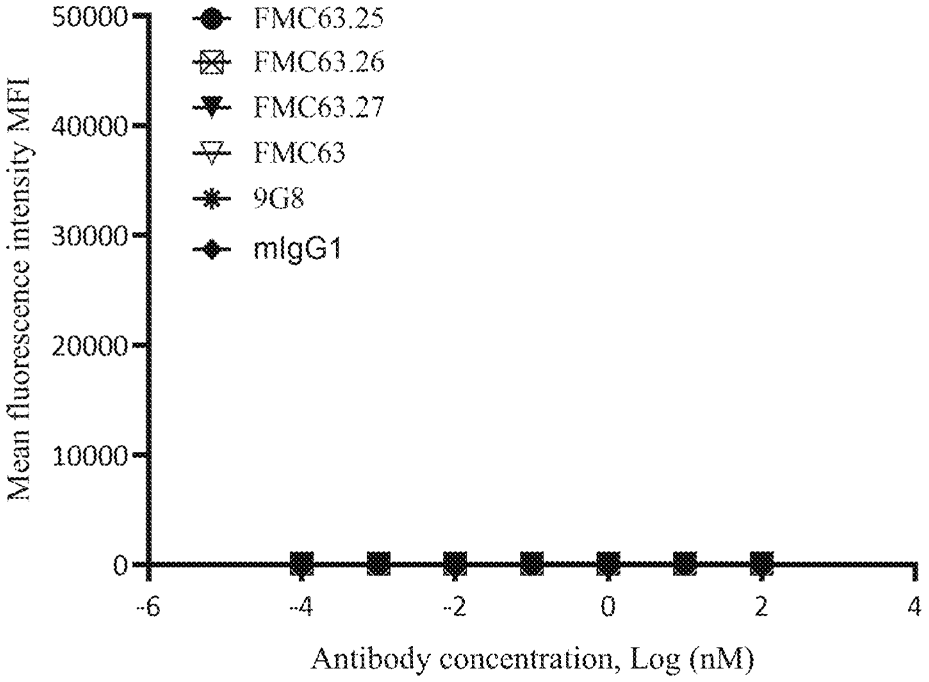
FIG. 9B shows assay results for binding reactions of humanized antibodies of FMC63 with HEK293T by FACS.

5.2 Assay on Binding of Humanized Antibodies of FMC63 to Monkey CD19-Expressing Cells by FACS HEK293T-monkey CD19 cells were subjected to the FACS assay and data analysis according to the method described in Example 4.2. The analysis results are shown in Table 12 and FIG. 9A, which show that FMC63.25 had good binding activity against 293T cells overexpressing monkey CD19, FMC63.26 had weak binding activity against 293T cells overexpressing monkey CD19, and FMC63.27 and FMC63 had weak binding activity against 293T cells overexpressing monkey CD19 only at the highest concentration. The same method was used to assay the binding of the humanized antibodies of FMC63 to HEK293T cells. The results are shown in FIG. 9B, which shows that the humanized antibodies of FMC63 all did not bind to HEK293T cells, having good specificity.

TABLE 12

Assay results for binding reactions of humanized antibodies of FMC63 with 293T-monkey CD19 cells by FACS

| Name of antibody | 293T-monkey CD19 Maximum mean fluorescence intensity | Ec50 (nM) |
|---|---|---|
| FMC63.25 | 34693 | 1.52 |
| FMC63.26 | 38495 | 20.32 |
| FMC63.27 | 11899 | 151.10 |
| FMC63 | 21341 | 125.90 |
| 9G8 | 19503 | 2.08 |
| mIgG1 | 165 | Negative |

Figure 10:
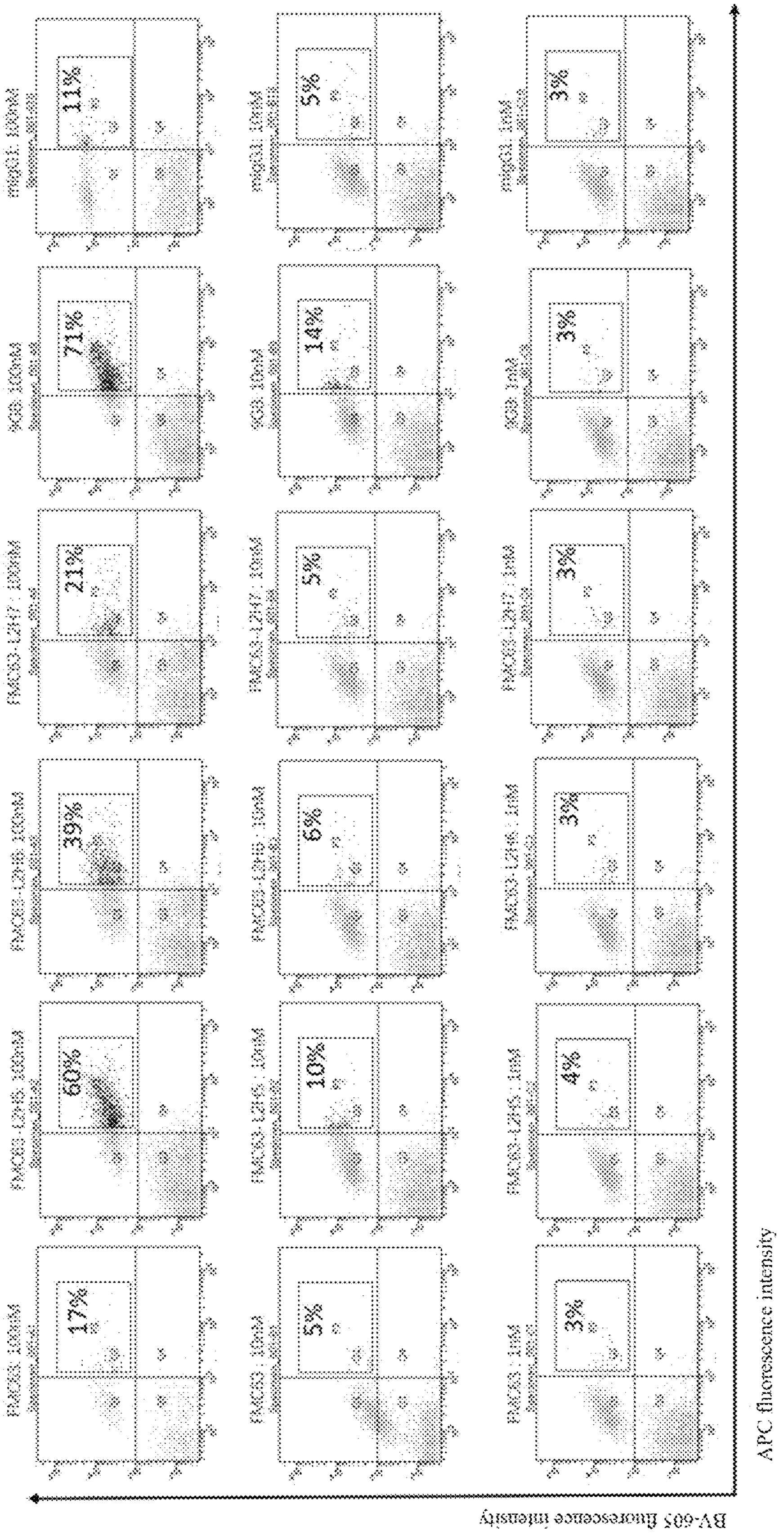
FIG. 10 shows assay results for binding reactions of humanized antibodies of FMC63 with cynomolgus monkey B cells by FACS, wherein FMC63-L2H5 is FMC63.25, FMC63-L2H6 is FMC63.26, and FMC63-L2H7 is FMC63.27.
Figure 11A:
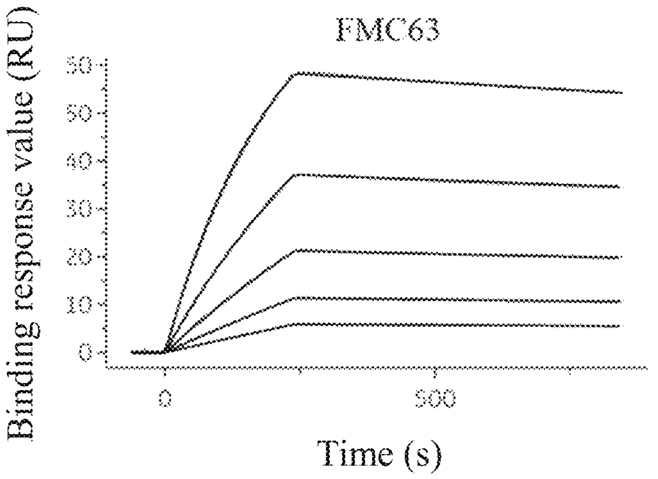
FIG. 11A shows assay results for affinity of FMC63 for a human CD19 protein by SPR.
Figure 11B:
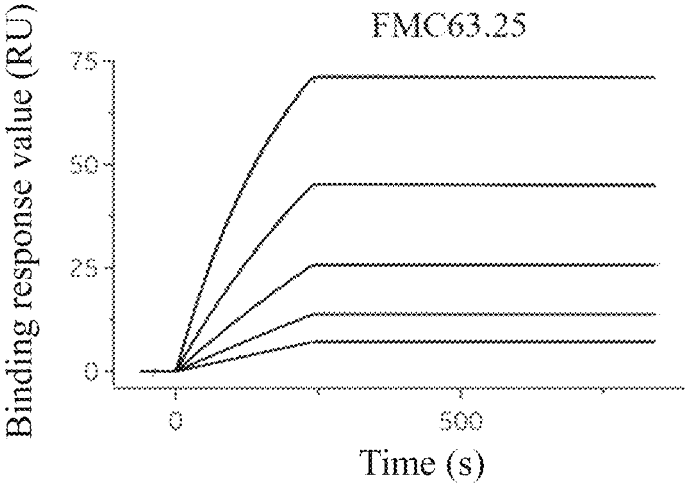
FIG. 11B shows assay results for affinity of humanized antibody FMC63.25 for a human CD19 protein by SPR.
Figure 11C:
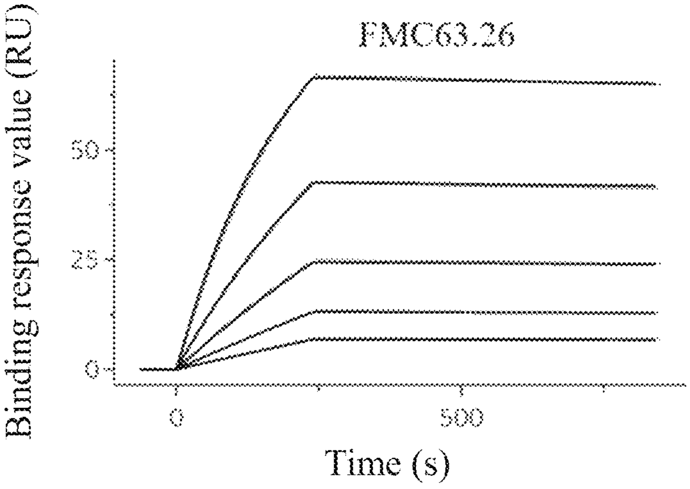
FIG. 11C shows assay results for affinity of humanized antibody FMC63.26 for a human CD19 protein by SPR.
Figure 11D:
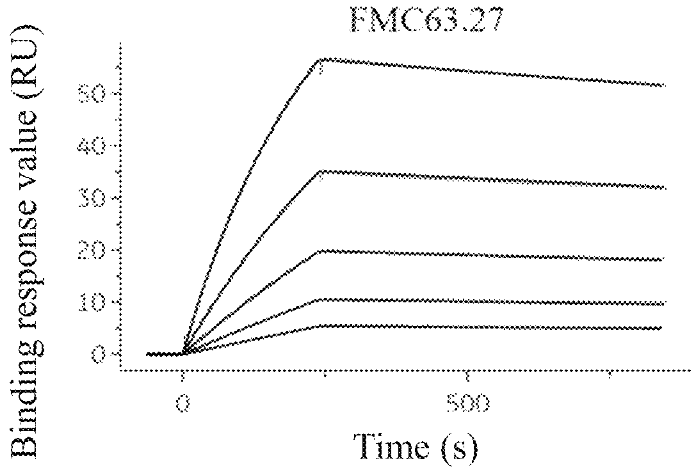
FIG. 11D shows assay results for affinity of humanized antibody FMC63.27 for a human CD19 protein by SPR.

5.3 Assay on Binding of Humanized Antibodies of FMC63 to Peripheral Blood B Cells of Cynomolgus Monkey (Latin Name: *Macaca fascicularis*) by FACS Monkey peripheral blood mononuclear cells were extracted from fresh cynomolgus monkey peripheral blood (purchased from Shanghai Medicilon Inc.) according to Ficoll-Paque Plus (purchased from GE Healthcare, Cat. No. 171440-02). The cell suspension was centrifuged, resuspended in PBS containing 1% BSA, and counted, and meanwhile, the murine antibody Brilliant Violet 605 anti-human CD20 (Cat. No. 302334, purchased from Biolegend) and the test humanized antibodies of FMC63 (1 nM, 10 nM, and 100 nM) were added. The cells were incubated at room temperature for 1 h. After the cells were washed three times, an Alexa Fluor 647-labeled secondary antibody anti-mouse IgG H+L (Cat. No. 115-605-003, purchased from Jackson Immuno) was added. The cells were incubated at room temperature for 30 min in the dark, washed 5 times, gently resuspended in PBS, and assayed and analyzed by FACS (FACS Canto™, purchased from BD Biosciences), in which CD20 was used as a marker for B cells. The CD20-positive B cell population was gated, the proportion of cells positive for the humanized antibodies of FMC63 was analyzed, and the proportions of positive cells after treatment with the humanized antibodies of FMC63 at concentrations of 100 nM, 10 nM and 1 nM, respectively, to the B cell population were calculated. The results are shown in Table 13. Double-stained cell scatter plots of the humanized antibodies of FMC63 indirectly labeled with Brilliant Violet 605-labeled CD20 and Alexa Fluor 647 secondary antibody are shown in FIG. 10. As can be seen from the results, FMC63.25 at a concentration of 100 nM bound to cynomolgus monkey B cells at a high proportion and had comparable or better binding activity as compared to the positive antibody 9G8; and other antibodies had no binding or weak binding to cynomolgus monkey CD19.

TABLE 13

Assay results for binding reactions of humanized antibodies of FMC63 with cynomolgus monkey B cells by FACS Proportion of cells positive for humanized antibodies of FMC63 to B cells (%)

| Name of antibody | Antibody concentration 100 nM | 10 nM | 1 nM |
|---|---|---|---|
| FMC63.25 | 60 | 10 | 4 |
| FMC63.26 | 39 | 6 | 3 |
| FMC63.27 | 21 | 5 | 3 |
| FMC63 | 17 | 5 | 3 |
| 9G8 | 71 | 14 | 3 |
| mIgG1 | 11 | 5 | 3 |

Example 6. Assay on Affinity of CD19 Antibody 6.1 Assay on Affinity of Humanized Antibodies for Human CD19-his Protein The anti-human CD19 antibody was captured using a Protein A chip (GE Healthcare; 29-127-558). The sample and running buffer was HBS-EP+ (10 mM HEPES, 150 mM NaCl, 3 mM EDTA, 0.05% surfactant P20) (GE Healthcare; BR-1006-69). The flow cell was set at 25° C. The sample block was set at 16° C. Both were pretreated with the running buffer. In each cycle, first, the test antibody was captured using the Protein A chip, and then a single concentration of CD19 antigen protein was injected. The association and dissociation processes of the antibody with the antigen protein were recorded, and finally, the chip was regenerated using Glycine pH 1.5 (GE Healthcare; BR-1003-54). The association was determined by injecting different concentrations of recombinant human CD19-His in the solution and maintaining for 240 s, wherein the flow rate was 30 μL/min, and the protein was diluted in a 1:1 dilution ratio from 200 nM (see detailed results for actual concentrations tested) to obtain 5 concentrations in total. The dissociation phase was monitored for up to 600 s and triggered by switching from the sample solution to the running buffer. The surface was regenerated by washing with 10 mM glycine solution (pH 1.5) at a flow rate of 30 μL/min for 30 s. The difference in bulk refractive index was corrected by subtracting the responses obtained from the goat anti-human Fc surface. Blank injections were also subtracted (double reference). To calculate the apparent KD and other kinetic parameters, the Langmuir 1:1 model was used. The association rate (Kon), dissociation rate (Koff), and binding affinity (KD) of the humanized antibodies of FMC63 with the human CD19-His protein are shown in Table 14, in which the antibody FMC63 was used as a control. As shown in FIG. 11 and Table 14, the humanized antibodies of FMC63 all bound to human CD19 with a KD of better than 2E-09 M, e.g., 1.81E-09, more preferably up to 3.46E-10, and most preferably up to 1.95E-11 M, showing the affinity comparable to or better than that of FMC63.

TABLE 14

Assay results for affinity of humanized antibodies of FMC63 for human CD19 by SPR (biacore)

| Name of antibody | ka (1/Ms) | kd (1/s) | KD (M) |
|---|---|---|---|
| FMC63.25 | 9.24E+04 | 1.80E−06 | 1.95E−11 |
| FMC63.26 | 9.72E+04 | 3.36E−05 | 3.46E−10 |
| FMC63.27 | 8.42E+04 | 1.52E−04 | 1.81E−09 |
| FMC63 | 9.53E+04 | 1.17E−04 | 1.23E−09 |

Figure 12:
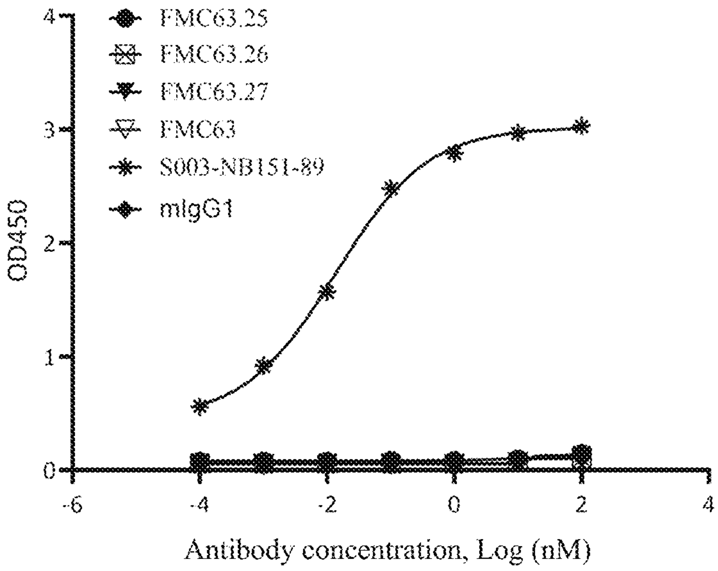
FIG. 12 shows assay results for binding reactions of humanized antibodies of FMC63 with a human CD19 exon1-3-his protein by ELISA.

Example 7. Identification of Binding Regions for Humanized Antibodies of FMC63 to Antigen The antigen-binding epitope for murine FMC63 is the membrane proximal external region (exon4-7) of the CD19 protein. To further confirm that the antigen-binding epitopes for the humanized antibodies remained unchanged, human CD19 exon1-3-His (membrane distal end) was coated at 2 μg/mL according to the ELISA method described in Example 4.1. As shown in FIG. 12 and Table 15, the humanized antibodies of FMC63 showed no binding activity against human CD19 exon1-3-His. Therefore, it can be determined that the antigen-binding epitopes for the humanized antibodies of FMC63 are the same as that of the parent antibody FMC63, and all of them are located at the membrane proximal external region of the CD19 protein (exon4-7).

TABLE 15

Classification of epitopes for humanized antibodies of FMC63

| Name of antibody | Binding region exon1-3 |
|---|---|
| FMC63.25 | — |
| FMC63.26 | — |
| FMC63.27 | — |
| FMC63 | — |

The invention claimed is:

1. A humanized antibody or antigen-binding fragment specifically binding to CD19, wherein the humanized antibody or the antigen-binding fragment comprises a heavy chain variable region set forth in SEQ ID NO: 8 and a light chain variable region set forth in SEQ ID NO: 7.

2. The antibody or the antigen-binding fragment according to claim 1, wherein the variable heavy domain ($V_H$) and the variable light domain ($V_L$) comprises CDR regions determined according to the Kabat numbering scheme, wherein, the HCDR1 is DYGVS; (SEQ ID NO: 22)

the HCDR2 is VIWGSETTYYNSALKS; (SEQ ID NO: 23)

the HCDR3 is HYYYGGSYAMDY; (SEQ ID NO: 24)

the HFR1 is QVTLKESGPVLVKPTETLTLTCTVSGFSLS; (SEQ ID NO: 25)

the HFR2 is WIRQPPGKALEWLA; (SEQ ID NO: 26)

the HFR3 is RLTISKDTSKSQVVLTMTNMDPVDTATYYCAR; (SEQ ID NO: 27)

the HFR4 is WGQGTTVTVSS; (SEQ ID NO: 4)

the LCDR1 is RASQDISKYLN; (SEQ ID NO: 28)

-continued the LCDR2 is HTSRLHS; (SEQ ID NO: 29)

the LCDR3 is QQGNTLPYT; (SEQ ID NO: 30)

the LFR1 is DIQMTQSPSSLSASVGDRVTITC; (SEQ ID NO: 31)

the LFR2 is WYQQKPGKAPKLLIY; (SEQ ID NO: 32)

the LFR3 is GVPSRFSGSGSGTDFTLTISSLQPEDFATYYC; and (SEQ ID NO: 33)

the LFR4 is FGGGTKVEIK. (SEQ ID NO: 6)

3. The antibody or the antigen-binding fragment according to claim 1, wherein the antibody or the antigen-binding fragment is selected from a monoclonal antibody, a polyclonal antibody, a natural antibody, an engineered antibody, a monospecific antibody, a multispecific antibody, a monovalent antibody, a multivalent antibody, a full-length antibody, an antibody fragment, a naked antibody, a conjugated antibody, a humanized antibody, a Fab, a Fab', a Fab'-SH, an $F(ab')_2$, an Fd, an Fv, an scFv, a diabody, and a single domain antibody.

4. The antibody or the antigen-binding fragment according to claim 1, wherein the antibody or the antigen-binding fragment comprises a heavy chain constant region and/or a light chain constant region, wherein the heavy chain constant region comprises a full-length heavy chain constant region or a fragment thereof, wherein the fragment can be selected from a CH1 domain, an Fc domain, and a CH3 domain;

the heavy chain constant region and/or the light chain constant region are a human heavy chain constant region and a human light chain constant region, respectively; and the heavy chain constant region is an IgG heavy chain constant region.

5. The antibody or the antigen-binding fragment according to claim 4, wherein the heavy chain constant region is selected from an IgG1 heavy chain constant region, an IgG2 heavy chain constant region, an IgG3 heavy chain constant region, and an IgG4 heavy chain constant region.

6. The antibody or the antigen-binding fragment according to claim 4, wherein the antibody or the antigen-binding fragment lacks fucosylation.

7. The antibody or the antigen-binding fragment according to claim 1, wherein the antibody or the antigen-binding fragment binds to human CD19 and/or monkey CD19; and optionally, the antibody or the antigen-binding fragment binds to human CD19 with a KD value of less than 1.00E-8 M, 1.00E-9 M, 2.00E-09 M, 3.00E-9 M, 4.00E-09 M, 5.00E-09 M, 6.00E-09 M, 7.00E-09 M, 8.00E-09 M, 9.00E-09 M, 1.00E-10 M, 2.00E-10 M, 3.00E-10 M, 4.00E-10 M, 5.00E-10 M, 6.00E-10 M, 7.00E-10 M, 8.00E-10 M, 9.00E-10 M, 1.00E-11 M, 2.00E-11 M, 3.00E-11 M, 4.00E-11 M, 5.00E-11 M, 6.00E-11 M, 7.00E-11 M, 8.00E-11 M, 9.00E-11 M, 1.00E-12 M, 2.00E-12 M, 3.00E-12 M, 4.00E-12 M, 5.00E-12 M, 6.00E-12 M, 7.00E-12 M, 8.00E-12 M, or 9.00E-12 M.

8. A chimeric antigen receptor (CAR), wherein the CAR comprises an extracellular antigen-binding domain, a transmembrane domain, and an intracellular signaling domain, wherein the extracellular antigen-binding domain comprises the CD19 antibody or the antigen-binding fragment according to claim 1.

9. An immune effector cell, wherein the immune effector cell comprises the chimeric antigen receptor according to claim 8 or a nucleic acid fragment encoding the chimeric antigen receptor according to claim 8, wherein the immune effector cell is selected from a T cell, an NK cell (natural killer cell), an NKT cell (natural killer T cell), a monocyte, a macrophage, a dendritic cell, and a mast cell, wherein the T cell can be selected from a cytotoxic T cell, a regulatory T cell (Treg), and a helper T cell; and wherein the immune effector cell is an allogeneic immune effector cell or an autologous immune effector cell.

10. A pharmaceutical composition, wherein the pharmaceutical composition comprises the antibody or the antigen-binding fragment according to claim 1 and a pharmaceutically acceptable carrier, diluent, or adjuvant.

11. A method for treating cancer or an autoimmune disease, wherein the method comprises administering to a subject an effective amount of the antibody according to claim 1, wherein the cancer is a lymphoma or leukemia selected from B-cell lymphoma, non-Hodgkin's lymphoma, mantle cell lymphoma, follicular lymphoma, marginal zone lymphoma, primary mediastinal B-cell lymphoma, diffuse large B-cell lymphoma, precursor B-cell acute lymphocytic leukemia (pre-B ALL), acute lymphocytic leukemia (ALL), chronic lymphocytic leukemia, hairy cell leukemia, prolymphocytic leukemia, plasmacytoma, Waldenstrom's tumor, and multiple myeloma; and wherein the autoimmune disease is selected from rheumatoid arthritis, multiple sclerosis, systemic sclerosis, neuromyelitis optica spectrum disease, systemic lupus erythematosus, myasthenia gravis, and an IgG4-related disease.

* * * * *

SEQUENCE LISTING

```
<160> NUMBER OF SEQ ID NOS: 56

<210> SEQ ID NO 1
<211> LENGTH: 107
<212> TYPE: PRT
<213> ORGANISM: Artificial sequence
<220> FEATURE:
<223> OTHER INFORMATION: synthesized polypeptide

<400> SEQUENCE: 1

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105


<210> SEQ ID NO 2
<211> LENGTH: 120
<212> TYPE: PRT
<213> ORGANISM: Artificial sequence
<220> FEATURE:
<223> OTHER INFORMATION: synthesized polypeptide

<400> SEQUENCE: 2
```

```
Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120


<210> SEQ ID NO 3
<211> LENGTH: 100
<212> TYPE: PRT
<213> ORGANISM: Artificial sequence
<220> FEATURE:
<223> OTHER INFORMATION: synthesized polypeptide

<400> SEQUENCE: 3

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile
            100


<210> SEQ ID NO 4
<211> LENGTH: 11
<212> TYPE: PRT
<213> ORGANISM: Artificial sequence
<220> FEATURE:
<223> OTHER INFORMATION: synthesized polypeptide

<400> SEQUENCE: 4

Trp Gly Gln Gly Thr Thr Val Thr Val Ser Ser
1               5                   10


<210> SEQ ID NO 5
<211> LENGTH: 95
<212> TYPE: PRT
<213> ORGANISM: Artificial sequence
<220> FEATURE:
<223> OTHER INFORMATION: synthesized polypeptide

<400> SEQUENCE: 5

Asp Ile Gln Met Thr Gln Ser Pro Ser Ser Leu Ser Ala Ser Val Gly
```

```
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95


<210> SEQ ID NO 6
<211> LENGTH: 10
<212> TYPE: PRT
<213> ORGANISM: Artificial sequence
<220> FEATURE:
<223> OTHER INFORMATION: synthesized polypeptide

<400> SEQUENCE: 6

Phe Gly Gly Gly Thr Lys Val Glu Ile Lys
1               5                   10


<210> SEQ ID NO 7
<211> LENGTH: 107
<212> TYPE: PRT
<213> ORGANISM: Artificial sequence
<220> FEATURE:
<223> OTHER INFORMATION: synthesized polypeptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Gly Ala Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gly Gly Thr Lys Val Glu Ile Lys
            100                 105


<210> SEQ ID NO 8
<211> LENGTH: 120
<212> TYPE: PRT
<213> ORGANISM: Artificial sequence
<220> FEATURE:
<223> OTHER INFORMATION: synthesized polypeptide

<400> SEQUENCE: 8

Glu Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asp Tyr
            20                  25                  30

Gly Val Ser Trp Ile Arg Gln Pro Pro Gly Lys Ala Leu Glu Trp Leu
        35                  40                  45
```

Ala Val Ile Trp Gly Ser Glu Thr Thr Tyr Tyr Asn Ser Ala Leu Lys
    50                  55                  60

Ser Arg Leu Thr Ile Ser Lys Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Thr Val Thr Val Ser Ser
        115                 120

<210> SEQ ID NO 9
<211> LENGTH: 120
<212> TYPE: PRT
<213> ORGANISM: Artificial sequence
<220> FEATURE:
<223> OTHER INFORMATION: synthesized polypeptide

<400> SEQUENCE: 9

Glu Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Pro Asp Tyr
            20                  25                  30

Gly Val Ser Trp Ile Arg Gln Pro Pro Gly Lys Ala Leu Glu Trp Leu
        35                  40                  45

Ala Val Ile Trp Gly Ser Glu Thr Thr Tyr Tyr Asn Ser Ala Leu Lys
    50                  55                  60

Ser Arg Leu Thr Ile Ser Lys Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Thr Val Thr Val Ser Ser
        115                 120

<210> SEQ ID NO 10
<211> LENGTH: 120
<212> TYPE: PRT
<213> ORGANISM: Artificial sequence
<220> FEATURE:
<223> OTHER INFORMATION: synthesized polypeptide

<400> SEQUENCE: 10

Glu Val Thr Leu Lys Glu Ser Gly Pro Val Leu Val Lys Pro Thr Glu
1               5                   10                  15

Thr Leu Thr Leu Thr Cys Thr Val Ser Gly Val Ser Leu Pro Asp Tyr
            20                  25                  30

Gly Val Ser Trp Ile Arg Gln Pro Pro Gly Lys Ala Leu Glu Trp Leu
        35                  40                  45

Ala Val Ile Trp Gly Ser Glu Thr Thr Tyr Tyr Asn Ser Ala Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Lys His Tyr Tyr Tyr Gly Gly Ser Tyr Ala Met Asp Tyr Trp Gly Gln

```
            100                 105                 110

Gly Thr Thr Val Thr Val Ser Ser
        115                 120


<210> SEQ ID NO 11
<211> LENGTH: 324
<212> TYPE: PRT
<213> ORGANISM: Mus musculus

<400> SEQUENCE: 11

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys


<210> SEQ ID NO 12
<211> LENGTH: 107
<212> TYPE: PRT
```

<213> ORGANISM: Mus musculus

<400> SEQUENCE: 12

```
Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```

<210> SEQ ID NO 13
<211> LENGTH: 167
<212> TYPE: PRT
<213> ORGANISM: Homo sapiens

<400> SEQUENCE: 13

```
Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Met Arg Pro Leu Ala Ile Trp Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
        115                 120                 125

Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln
                165
```

<210> SEQ ID NO 14
<211> LENGTH: 444
<212> TYPE: PRT
<213> ORGANISM: Artificial sequence
<220> FEATURE:
<223> OTHER INFORMATION: synthesized polypeptide

<400> SEQUENCE: 14

```
Glu Val Lys Leu Gln Glu Ser Gly Pro Gly Leu Val Ala Pro Ser Gln
1               5                   10                  15
```

-continued

```
Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
```

```
        435                 440


<210> SEQ ID NO 15
<211> LENGTH: 214
<212> TYPE: PRT
<213> ORGANISM: Artificial sequence
<220> FEATURE:
<223> OTHER INFORMATION: synthesized polypeptide

<400> SEQUENCE: 15

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 16
<211> LENGTH: 122
<212> TYPE: PRT
<213> ORGANISM: Artificial sequence
<220> FEATURE:
<223> OTHER INFORMATION: synthesized polypeptide

<400> SEQUENCE: 16

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80
```

```
Leu Gln Trp Ser Ser Leu Lys Ala Ser Asp Thr Ala Met Tyr Tyr Cys
                85                  90                  95

Ala Arg Gly Val Ser Gly Ile Tyr Asn Leu His Gly Phe Asp Ile Trp
            100                 105                 110

Gly Gln Gly Thr Leu Val Thr Val Ser Ser
        115                 120


<210> SEQ ID NO 17
<211> LENGTH: 446
<212> TYPE: PRT
<213> ORGANISM: Artificial sequence
<220> FEATURE:
<223> OTHER INFORMATION: synthesized polypeptide

<400> SEQUENCE: 17

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Val Ser Gly Ile Tyr Asn Leu His Gly Phe Asp Ile Trp
            100                 105                 110

Gly Gln Gly Thr Leu Val Thr Val Ser Ser Ala Lys Thr Thr Pro Pro
        115                 120                 125

Ser Val Tyr Pro Leu Ala Pro Gly Ser Ala Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Pro Ser Ser Thr Trp Pro Ser Glu Thr Val Thr Cys Asn Val Ala His
        195                 200                 205

Pro Ala Ser Ser Thr Lys Val Asp Lys Lys Ile Val Pro Arg Asp Cys
    210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
        275                 280                 285

Gln Pro Arg Glu Glu Gln Phe Asn Ser Thr Phe Arg Ser Val Ser Glu
    290                 295                 300

Leu Pro Ile Met His Gln Asp Trp Leu Asn Gly Lys Glu Phe Lys Cys
305                 310                 315                 320
```

Arg Val Asn Ser Ala Ala Phe Pro Ala Pro Ile Glu Lys Thr Ile Ser
325 330 335

Lys Thr Lys Gly Arg Pro Lys Ala Pro Gln Val Tyr Thr Ile Pro Pro
340 345 350

Pro Lys Glu Gln Met Ala Lys Asp Lys Val Ser Leu Thr Cys Met Ile
355 360 365

Thr Asp Phe Phe Pro Glu Asp Ile Thr Val Glu Trp Gln Trp Asn Gly
370 375 380

Gln Pro Ala Glu Asn Tyr Lys Asn Thr Gln Pro Ile Met Asp Thr Asp
385 390 395 400

Gly Ser Tyr Phe Val Tyr Ser Lys Leu Asn Val Gln Lys Ser Asn Trp
405 410 415

Glu Ala Gly Asn Thr Phe Thr Cys Ser Val Leu His Glu Gly Leu His
420 425 430

Asn His His Thr Glu Lys Ser Leu Ser His Ser Pro Gly Lys
435 440 445

<210> SEQ ID NO 18
<211> LENGTH: 108
<212> TYPE: PRT
<213> ORGANISM: Artificial sequence
<220> FEATURE:
<223> OTHER INFORMATION: synthesized polypeptide

<400> SEQUENCE: 18

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Gly Arg Phe Gly Ser Pro
85 90 95

Phe Thr Phe Gly Gln Gly Thr Lys Val Glu Ile Lys
100 105

<210> SEQ ID NO 19
<211> LENGTH: 215
<212> TYPE: PRT
<213> ORGANISM: Artificial sequence
<220> FEATURE:
<223> OTHER INFORMATION: synthesized polypeptide

<400> SEQUENCE: 19

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

```
Glu Asp Phe Ala Thr Tyr Tyr Cys Gln Gln Gly Arg Phe Gly Ser Pro
                85                  90                  95

Phe Thr Phe Gly Gln Gly Thr Lys Val Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215


<210> SEQ ID NO 20
<211> LENGTH: 556
<212> TYPE: PRT
<213> ORGANISM: Homo sapiens

<400> SEQUENCE: 20

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
```

```
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
        515                 520                 525

Asp Ser Tyr Glu Asn Met Asp Asn Pro Asp Gly Pro Asp Pro Ala Trp
    530                 535                 540

Gly Gly Gly Gly Arg Met Gly Thr Trp Ser Thr Arg
545                 550                 555


<210> SEQ ID NO 21
<211> LENGTH: 557
<212> TYPE: PRT
<213> ORGANISM: Macaca mulatta

<400> SEQUENCE: 21

Met Pro Pro Pro Cys Leu Leu Phe Phe Leu Leu Phe Leu Thr Pro Met
1               5                   10                  15

Glu Val Arg Pro Gln Glu Pro Leu Val Val Lys Val Glu Glu Gly Asp
            20                  25                  30

Asn Ala Val Leu Gln Cys Leu Glu Gly Thr Ser Asp Gly Pro Thr Gln
        35                  40                  45
```

-continued

```
Gln Leu Val Trp Cys Arg Asp Ser Pro Phe Glu Pro Phe Leu Asn Leu
    50                  55                  60

Ser Leu Gly Leu Pro Gly Met Gly Ile Arg Met Gly Pro Leu Gly Ile
65                  70                  75                  80

Trp Leu Leu Ile Phe Asn Val Ser Asn Gln Thr Gly Gly Phe Tyr Leu
                85                  90                  95

Cys Gln Pro Gly Leu Pro Ser Glu Lys Ala Trp Gln Pro Gly Trp Thr
            100                 105                 110

Val Ser Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Asn Ser Ser Gln Leu Tyr Val Trp Ala
145                 150                 155                 160

Lys Asp Arg Pro Glu Met Trp Glu Gly Glu Pro Val Cys Gly Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val Arg Pro Lys Gly Pro Lys Ser
    210                 215                 220

Ser Leu Leu Ser Leu Glu Leu Lys Asp Asp Arg Pro Asp Arg Asp Met
225                 230                 235                 240

Trp Val Val Asp Thr Gly Leu Leu Leu Thr Arg Ala Thr Ala Gln Asp
                245                 250                 255

Ala Gly Lys Tyr Tyr Cys His Arg Gly Asn Trp Thr Lys Ser Phe Tyr
            260                 265                 270

Leu Glu Ile Thr Ala Arg Pro Ala Leu Trp His Trp Leu Leu Arg Ile
        275                 280                 285

Gly Gly Trp Lys Val Pro Ala Val Thr Leu Thr Tyr Leu Ile Phe Cys
    290                 295                 300

Leu Cys Ser Leu Val Gly Ile Leu Gln Leu Gln Arg Ala Leu Val Leu
305                 310                 315                 320

Arg Arg Lys Arg Lys Arg Met Thr Asp Pro Thr Arg Arg Phe Phe Lys
                325                 330                 335

Val Thr Pro Pro Pro Gly Ser Gly Pro Gln Asn Gln Tyr Gly Asn Val
            340                 345                 350

Leu Ser Leu Pro Thr Pro Thr Ser Gly Leu Gly Arg Ala Gln Arg Trp
        355                 360                 365

Ala Ala Gly Leu Gly Gly Thr Ala Pro Ser Tyr Gly Asn Pro Ser Ser
    370                 375                 380

Asp Val Gln Val Asp Gly Ala Val Gly Ser Arg Ser Pro Pro Gly Ala
385                 390                 395                 400

Gly Pro Glu Glu Glu Glu Gly Glu Gly Tyr Glu Glu Pro Asp Ser Glu
                405                 410                 415

Glu Gly Ser Glu Phe Tyr Glu Asn Asp Ser Asn Phe Gly Gln Asp Gln
            420                 425                 430

Leu Ser Gln Asp Gly Ser Gly Tyr Glu Asn Pro Glu Asp Glu Pro Leu
        435                 440                 445

Gly Pro Glu Asp Glu Asp Ser Phe Ser Asn Ala Glu Ser Tyr Glu Asn
    450                 455                 460

Glu Asp Glu Glu Leu Thr Gln Pro Val Ala Arg Thr Met Asp Phe Leu
```

```
465                 470                 475                 480

Ser Pro His Gly Ser Ala Trp Asp Pro Ser Arg Glu Ala Thr Ser Leu
                485                 490                 495

Gly Ser Gln Ser Tyr Glu Asp Met Arg Gly Leu Leu Tyr Ala Ala Pro
            500                 505                 510

Gln Leu Arg Thr Ile Arg Gly Gln Pro Gly Pro Asn His Glu Glu Asp
        515                 520                 525

Ala Asp Ser Tyr Glu Asn Met Asp Asn Pro Asp Gly Pro Asp Pro Ala
    530                 535                 540

Trp Gly Gly Gly Gly Arg Met Gly Thr Trp Ser Ala Arg
545                 550                 555


<210> SEQ ID NO 22
<211> LENGTH: 5
<212> TYPE: PRT
<213> ORGANISM: Artificial sequence
<220> FEATURE:
<223> OTHER INFORMATION: synthesized polypeptide

<400> SEQUENCE: 22

Asp Tyr Gly Val Ser
1               5


<210> SEQ ID NO 23
<211> LENGTH: 16
<212> TYPE: PRT
<213> ORGANISM: Artificial sequence
<220> FEATURE:
<223> OTHER INFORMATION: synthesized polypeptide

<400> SEQUENCE: 23

Val Ile Trp Gly Ser Glu Thr Thr Tyr Tyr Asn Ser Ala Leu Lys Ser
1               5                   10                  15


<210> SEQ ID NO 24
<211> LENGTH: 12
<212> TYPE: PRT
<213> ORGANISM: Artificial sequence
<220> FEATURE:
<223> OTHER INFORMATION: synthesized polypeptide

<400> SEQUENCE: 24

His Tyr Tyr Tyr Gly Gly Ser Tyr Ala Met Asp Tyr
1               5                   10


<210> SEQ ID NO 25
<211> LENGTH: 30
<212> TYPE: PRT
<213> ORGANISM: Artificial sequence
<220> FEATURE:
<223> OTHER INFORMATION: synthesized polypeptide

<400> SEQUENCE: 25

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser
            20                  25                  30


<210> SEQ ID NO 26
<211> LENGTH: 14
<212> TYPE: PRT
<213> ORGANISM: Artificial sequence
<220> FEATURE:
<223> OTHER INFORMATION: synthesized polypeptide
```

<400> SEQUENCE: 26

Trp Ile Arg Gln Pro Pro Gly Lys Ala Leu Glu Trp Leu Ala
1 5 10

<210> SEQ ID NO 27
<211> LENGTH: 32
<212> TYPE: PRT
<213> ORGANISM: Artificial sequence
<220> FEATURE:
<223> OTHER INFORMATION: synthesized polypeptide

<400> SEQUENCE: 27

Arg Leu Thr Ile Ser Lys Asp Thr Ser Lys Ser Gln Val Val Leu Thr
1 5 10 15

Met Thr Asn Met Asp Pro Val Asp Thr Ala Thr Tyr Tyr Cys Ala Arg
20 25 30

<210> SEQ ID NO 28
<211> LENGTH: 11
<212> TYPE: PRT
<213> ORGANISM: Artificial sequence
<220> FEATURE:
<223> OTHER INFORMATION: synthesized polypeptide

<400> SEQUENCE: 28

Arg Ala Ser Gln Asp Ile Ser Lys Tyr Leu Asn
1 5 10

<210> SEQ ID NO 29
<211> LENGTH: 7
<212> TYPE: PRT
<213> ORGANISM: Artificial sequence
<220> FEATURE:
<223> OTHER INFORMATION: synthesized polypeptide

<400> SEQUENCE: 29

His Thr Ser Arg Leu His Ser
1 5

<210> SEQ ID NO 30
<211> LENGTH: 9
<212> TYPE: PRT
<213> ORGANISM: Artificial sequence
<220> FEATURE:
<223> OTHER INFORMATION: synthesized polypeptide

<400> SEQUENCE: 30

Gln Gln Gly Asn Thr Leu Pro Tyr Thr
1 5

<210> SEQ ID NO 31
<211> LENGTH: 23
<212> TYPE: PRT
<213> ORGANISM: Artificial sequence
<220> FEATURE:
<223> OTHER INFORMATION: synthesized polypeptide

<400> SEQUENCE: 31

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 32

<211> LENGTH: 15
<212> TYPE: PRT
<213> ORGANISM: Artificial sequence
<220> FEATURE:
<223> OTHER INFORMATION: synthesized polypeptide

<400> SEQUENCE: 32

Trp Tyr Gln Gln Lys Pro Gly Lys Ala Pro Lys Leu Leu Ile Tyr
1 5 10 15

<210> SEQ ID NO 33
<211> LENGTH: 32
<212> TYPE: PRT
<213> ORGANISM: Artificial sequence
<220> FEATURE:
<223> OTHER INFORMATION: synthesized polypeptide

<400> SEQUENCE: 33

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 34
<211> LENGTH: 7
<212> TYPE: PRT
<213> ORGANISM: Artificial sequence
<220> FEATURE:
<223> OTHER INFORMATION: synthesized polypeptide

<400> SEQUENCE: 34

Gly Val Ser Leu Pro Asp Tyr
1 5

<210> SEQ ID NO 35
<211> LENGTH: 7
<212> TYPE: PRT
<213> ORGANISM: Artificial sequence
<220> FEATURE:
<223> OTHER INFORMATION: synthesized polypeptide

<400> SEQUENCE: 35

Gly Phe Ser Leu Ser Asp Tyr
1 5

<210> SEQ ID NO 36
<211> LENGTH: 7
<212> TYPE: PRT
<213> ORGANISM: Artificial sequence
<220> FEATURE:
<223> OTHER INFORMATION: synthesized polypeptide

<400> SEQUENCE: 36

Gly Phe Ser Leu Pro Asp Tyr
1 5

<210> SEQ ID NO 37
<211> LENGTH: 5
<212> TYPE: PRT
<213> ORGANISM: Artificial sequence
<220> FEATURE:
<223> OTHER INFORMATION: synthesized polypeptide

<400> SEQUENCE: 37

Trp Gly Ser Glu Thr
1 5

<210> SEQ ID NO 38
<211> LENGTH: 25
<212> TYPE: PRT
<213> ORGANISM: Artificial sequence
<220> FEATURE:
<223> OTHER INFORMATION: synthesized polypeptide

<400> SEQUENCE: 38

```
Gln Val Thr Leu Lys Glu Ser Gly Pro Val Leu Val Lys Pro Thr Glu
1               5                   10                  15

Thr Leu Thr Leu Thr Cys Thr Val Ser
            20                  25
```

<210> SEQ ID NO 39
<211> LENGTH: 19
<212> TYPE: PRT
<213> ORGANISM: Artificial sequence
<220> FEATURE:
<223> OTHER INFORMATION: synthesized polypeptide

<400> SEQUENCE: 39

```
Gly Val Ser Trp Ile Arg Gln Pro Pro Gly Lys Ala Leu Glu Trp Leu
1               5                   10                  15

Ala His Ile
```

<210> SEQ ID NO 40
<211> LENGTH: 41
<212> TYPE: PRT
<213> ORGANISM: Artificial sequence
<220> FEATURE:
<223> OTHER INFORMATION: synthesized polypeptide

<400> SEQUENCE: 40

```
Lys Ser Tyr Ser Thr Ser Leu Lys Ser Arg Leu Thr Ile Ser Lys Asp
1               5                   10                  15

Thr Ser Lys Ser Gln Val Val Leu Thr Met Thr Asn Met Asp Pro Val
            20                  25                  30

Asp Thr Ala Thr Tyr Tyr Cys Ala Arg
        35                  40
```

<210> SEQ ID NO 41
<211> LENGTH: 8
<212> TYPE: PRT
<213> ORGANISM: Artificial sequence
<220> FEATURE:
<223> OTHER INFORMATION: synthesized polypeptide

<400> SEQUENCE: 41

```
Gly Val Ser Leu Pro Asp Tyr Gly
1               5
```

<210> SEQ ID NO 42
<211> LENGTH: 8
<212> TYPE: PRT
<213> ORGANISM: Artificial sequence
<220> FEATURE:
<223> OTHER INFORMATION: synthesized polypeptide

<400> SEQUENCE: 42

```
Gly Phe Ser Leu Ser Asp Tyr Gly
1               5
```

<210> SEQ ID NO 43
<211> LENGTH: 8

<212> TYPE: PRT
<213> ORGANISM: Artificial sequence
<220> FEATURE:
<223> OTHER INFORMATION: synthesized polypeptide

<400> SEQUENCE: 43

Gly Phe Ser Leu Pro Asp Tyr Gly
1               5

<210> SEQ ID NO 44
<211> LENGTH: 7
<212> TYPE: PRT
<213> ORGANISM: Artificial sequence
<220> FEATURE:
<223> OTHER INFORMATION: synthesized polypeptide

<400> SEQUENCE: 44

Ile Trp Gly Ser Glu Thr Thr
1               5

<210> SEQ ID NO 45
<211> LENGTH: 14
<212> TYPE: PRT
<213> ORGANISM: Artificial sequence
<220> FEATURE:
<223> OTHER INFORMATION: synthesized polypeptide

<400> SEQUENCE: 45

Ala Lys His Tyr Tyr Tyr Gly Gly Ser Tyr Ala Met Asp Tyr
1               5                   10

<210> SEQ ID NO 46
<211> LENGTH: 17
<212> TYPE: PRT
<213> ORGANISM: Artificial sequence
<220> FEATURE:
<223> OTHER INFORMATION: synthesized polypeptide

<400> SEQUENCE: 46

Val Ser Trp Ile Arg Gln Pro Pro Gly Lys Ala Leu Glu Trp Leu Ala
1               5                   10                  15

His

<210> SEQ ID NO 47
<211> LENGTH: 38
<212> TYPE: PRT
<213> ORGANISM: Artificial sequence
<220> FEATURE:
<223> OTHER INFORMATION: synthesized polypeptide

<400> SEQUENCE: 47

Ser Tyr Ser Thr Ser Leu Lys Ser Arg Leu Thr Ile Ser Lys Asp Thr
1               5                   10                  15

Ser Lys Ser Gln Val Val Leu Thr Met Thr Asn Met Asp Pro Val Asp
            20                  25                  30

Thr Ala Thr Tyr Tyr Cys
        35

<210> SEQ ID NO 48
<211> LENGTH: 6
<212> TYPE: PRT
<213> ORGANISM: Artificial sequence
<220> FEATURE:
<223> OTHER INFORMATION: synthesized polypeptide

<400> SEQUENCE: 48

Gln Asp Ile Ser Lys Tyr
1 5

<210> SEQ ID NO 49

<400> SEQUENCE: 49

000

<210> SEQ ID NO 50

<400> SEQUENCE: 50

000

<210> SEQ ID NO 51
<211> LENGTH: 26
<212> TYPE: PRT
<213> ORGANISM: Artificial sequence
<220> FEATURE:
<223> OTHER INFORMATION: synthesized polypeptide

<400> SEQUENCE: 51

Asp Ile Gln Met Thr Gln Ser Pro Ser Ser Leu Ser Ala Ser Val Gly
1 5 10 15

Asp Arg Val Thr Ile Thr Cys Arg Ala Ser
20 25

<210> SEQ ID NO 52
<211> LENGTH: 17
<212> TYPE: PRT
<213> ORGANISM: Artificial sequence
<220> FEATURE:
<223> OTHER INFORMATION: synthesized polypeptide

<400> SEQUENCE: 52

Leu Asn Trp Tyr Gln Gln Lys Pro Gly Lys Ala Pro Lys Leu Leu Ile
1 5 10 15

Tyr

<210> SEQ ID NO 53
<211> LENGTH: 37
<212> TYPE: PRT
<213> ORGANISM: Artificial sequence
<220> FEATURE:
<223> OTHER INFORMATION: synthesized polypeptide

<400> SEQUENCE: 53

Ser Ser Leu Gln Ser Gly Val Pro Ser Arg Phe Ser Gly Ser Gly Ser
1 5 10 15

Gly Thr Asp Phe Thr Leu Thr Ile Ser Ser Leu Gln Pro Glu Asp Phe
20 25 30

Ala Thr Tyr Tyr Cys
35

<210> SEQ ID NO 54
<211> LENGTH: 36
<212> TYPE: PRT
<213> ORGANISM: Artificial sequence
<220> FEATURE:
<223> OTHER INFORMATION: synthesized polypeptide

<400> SEQUENCE: 54

Ser Leu Gln Ser Gly Val Pro Ser Arg Phe Ser Gly Ser Gly Ser Gly

-continued

```
1               5                   10                  15

Thr Asp Phe Thr Leu Thr Ile Ser Ser Leu Gln Pro Glu Asp Phe Ala
            20                  25                  30

Thr Tyr Tyr Cys
        35


<210> SEQ ID NO 55
<211> LENGTH: 5
<212> TYPE: PRT
<213> ORGANISM: Artificial sequence
<220> FEATURE:
<223> OTHER INFORMATION: Synthetic Construct

<400> SEQUENCE: 55

Gly Gly Gly Gly Ser
1               5


<210> SEQ ID NO 56
<211> LENGTH: 20
<212> TYPE: PRT
<213> ORGANISM: Artificial sequence
<220> FEATURE:
<223> OTHER INFORMATION: Synthetic Construct

<400> SEQUENCE: 56

Gly Gly Gly Gly Ser Gly Gly Gly Gly Ser Gly Gly Gly Gly Ser Gly
1               5                   10                  15

Gly Gly Gly Ser
            20
```